US010765822B2

(12) United States Patent
Dong et al.

(10) Patent No.: US 10,765,822 B2
(45) Date of Patent: Sep. 8, 2020

(54) ENDOTRACHEAL TUBE EXTUBATION DETECTION

(71) Applicant: Covidien LP, Mansfield, MA (US)

(72) Inventors: Nancy F. Dong, Carlsbad, CA (US); Gabriel Sanchez, Valley Center, CA (US)

(73) Assignee: COVIDIEN LP, Mansfield, MA (US)

(*) Notice: Subject to any disclaimer, the term of this patent is extended or adjusted under 35 U.S.C. 154(b) by 579 days.

(21) Appl. No.: 15/489,315

(22) Filed: Apr. 17, 2017

(65) Prior Publication Data
US 2017/0296765 A1    Oct. 19, 2017

Related U.S. Application Data

(60) Provisional application No. 62/324,108, filed on Apr. 18, 2016.

(51) Int. Cl.
*A61M 16/00* (2006.01)
*A61M 16/04* (2006.01)
*A61M 16/08* (2006.01)

(52) U.S. Cl.
CPC ........ *A61M 16/0051* (2013.01); *A61M 16/04* (2013.01); *A61M 16/0833* (2014.02); *A61M 16/0063* (2014.02); *A61M 2016/0027* (2013.01); *A61M 2016/0036* (2013.01); *A61M 2205/13* (2013.01); *A61M 2205/14* (2013.01); *A61M 2205/18* (2013.01); *A61M 2205/502* (2013.01);
(Continued)

(58) Field of Classification Search
CPC .............................. A61M 16/0051; A61B 5/08
See application file for complete search history.

(56) References Cited

U.S. PATENT DOCUMENTS 4,550,726 A    11/1985 McEwen
4,752,089 A     6/1988 Carter
(Continued)

FOREIGN PATENT DOCUMENTS

CN        204406612 U    6/2015
CN        204406613 U    6/2015
WO    WO 2013149138 A1   10/2013

OTHER PUBLICATIONS

7200 Series Ventilator, Options, and Accessories: Operator's Manual. Nellcor Puritan Bennett, Part No. 22300 A, Sep. 1990, pp. 1-196.
(Continued)

*Primary Examiner* — Timothy A Stanis
*Assistant Examiner* — Cana A Gallegos

(57) ABSTRACT

Systems and methods for detecting extubation of an endotracheal tube (ETT) are described. Extubation of the ETT can be identified by comparing to a threshold, a difference between a determined first volume of breathing gas during a first inspiratory period to a determined second volume of breathing gas during a second inspiratory period. If the difference exceeds the threshold, an alarm can be activated indicating extubation. Extubation detection may also be based on a difference between inspiratory pressures during separate inspiratory periods. Partial extubation and full extubation may also be discerned. Further, extubation of an ETT may be detected without the use of an exhalation flow sensor.

15 Claims, 11 Drawing Sheets
(4 of 11 Drawing Sheet(s) Filed in Color)

(52) U.S. Cl.
CPC ..... *A61M 2205/52* (2013.01); *A61M 2240/00* (2013.01)

(56) References Cited

U.S. PATENT DOCUMENTS

| | | | |
|---|---|---|---|
| 4,921,642 A | 5/1990 | LaTorraca |
| 4,954,799 A | 9/1990 | Kumar |
| 4,978,323 A | 12/1990 | Freedman |
| 5,057,822 A | 10/1991 | Hoffman |
| 5,072,737 A | 12/1991 | Goulding |
| 5,150,291 A | 9/1992 | Cummings et al. |
| 5,161,525 A | 11/1992 | Kimm et al. |
| 5,237,987 A | 8/1993 | Anderson et al. |
| 5,271,389 A | 12/1993 | Isaza et al. |
| 5,279,549 A | 1/1994 | Ranford |
| 5,299,568 A | 4/1994 | Forare et al. |
| 5,301,921 A | 4/1994 | Kumar |
| 5,319,540 A | 6/1994 | Isaza et al. |
| 5,325,861 A | 7/1994 | Goulding |
| 5,333,606 A | 8/1994 | Schneider et al. |
| 5,339,807 A | 8/1994 | Carter |
| 5,343,857 A | 9/1994 | Schneider et al. |
| 5,351,522 A | 10/1994 | Lura |
| 5,357,946 A | 10/1994 | Kee et al. |
| 5,368,019 A | 11/1994 | LaTorraca |
| 5,383,449 A | 1/1995 | Forare et al. |
| 5,385,142 A | 1/1995 | Brady et al. |
| 5,390,666 A | 2/1995 | Kimm et al. |
| 5,401,135 A | 3/1995 | Stoen et al. |
| 5,402,796 A | 4/1995 | Packer et al. |
| 5,407,174 A | 4/1995 | Kumar |
| 5,413,110 A | 5/1995 | Cummings et al. |
| 5,438,980 A | 8/1995 | Phillips |
| 5,443,075 A | 8/1995 | Holscher |
| 5,513,631 A | 5/1996 | McWilliams |
| 5,517,983 A | 5/1996 | Deighan et al. |
| 5,520,071 A | 5/1996 | Jones |
| 5,524,615 A | 6/1996 | Power |
| 5,531,221 A | 7/1996 | Power |
| 5,542,415 A | 8/1996 | Brody |
| 5,544,674 A | 8/1996 | Kelly |
| 5,549,106 A | 8/1996 | Gruenke et al. |
| 5,596,984 A | 1/1997 | O'Mahony et al. |
| 5,630,411 A | 5/1997 | Holscher |
| 5,632,270 A | 5/1997 | O'Mahony et al. |
| 5,645,048 A | 7/1997 | Brodsky et al. |
| 5,660,171 A | 8/1997 | Kimm et al. |
| 5,664,560 A | 9/1997 | Merrick et al. |
| 5,664,562 A | 9/1997 | Bourdon |
| 5,671,767 A | 9/1997 | Kelly |
| 5,672,041 A | 9/1997 | Ringdahl et al. |
| 5,673,689 A | 10/1997 | Power |
| 5,715,812 A | 2/1998 | Deighan et al. |
| 5,762,480 A | 6/1998 | Adahan |
| 5,771,884 A | 6/1998 | Yarnall et al. |
| 5,791,339 A | 8/1998 | Winter |
| 5,794,986 A | 8/1998 | Gansel et al. |
| 5,813,399 A | 9/1998 | Isaza et al. |
| 5,826,575 A | 10/1998 | Lall |
| 5,829,441 A | 11/1998 | Kidd et al. |
| 5,864,938 A | 2/1999 | Gansel et al. |
| 5,865,168 A | 2/1999 | Isaza |
| 5,881,717 A * | 3/1999 | Isaza ................ A61M 16/0051 128/202.22 |
| 5,881,723 A | 3/1999 | Wallace et al. |
| 5,884,623 A | 3/1999 | Winter |
| 5,909,731 A | 6/1999 | O'Mahony et al. |
| 5,915,379 A | 6/1999 | Wallace et al. |
| 5,915,380 A | 6/1999 | Wallace et al. |
| 5,915,382 A | 6/1999 | Power |
| 5,918,597 A | 7/1999 | Jones et al. |
| 5,921,238 A | 7/1999 | Bourdon |
| 5,934,274 A | 8/1999 | Merrick et al. |
| 6,024,089 A | 2/2000 | Wallace et al. |
| 6,041,780 A | 3/2000 | Richard et al. |
| 6,047,860 A | 4/2000 | Sanders |
| 6,076,523 A | 6/2000 | Jones et al. |
| 6,116,240 A | 9/2000 | Merrick et al. |
| 6,116,464 A | 9/2000 | Sanders |
| 6,123,073 A | 9/2000 | Schlawin et al. |
| 6,135,106 A | 10/2000 | Dirks et al. |
| 6,142,150 A | 11/2000 | O'Mahony et al. |
| 6,161,539 A | 12/2000 | Winter |
| 6,213,119 B1 | 4/2001 | Brydon et al. |
| 6,220,245 B1 | 4/2001 | Takabayashi et al. |
| 6,269,812 B1 | 8/2001 | Wallace et al. |
| 6,273,444 B1 | 8/2001 | Power |
| 6,283,119 B1 | 9/2001 | Bourdon |
| 6,305,373 B1 | 10/2001 | Wallace et al. |
| 6,321,748 B1 | 11/2001 | O'Mahoney |
| 6,325,785 B1 | 12/2001 | Babkes et al. |
| 6,357,438 B1 | 3/2002 | Hansen |
| 6,360,745 B1 | 3/2002 | Wallace et al. |
| 6,369,838 B1 | 4/2002 | Wallace et al. |
| 6,412,483 B1 | 7/2002 | Jones et al. |
| 6,439,229 B1 | 8/2002 | Du et al. |
| 6,467,478 B1 | 10/2002 | Merrick et al. |
| 6,546,930 B1 | 4/2003 | Emerson et al. |
| 6,553,991 B1 | 4/2003 | Isaza |
| 6,557,553 B1 | 5/2003 | Borrello |
| 6,571,795 B2 | 6/2003 | Bourdon |
| 6,622,726 B1 | 9/2003 | Du |
| 6,644,310 B1 | 11/2003 | Delache et al. |
| 6,668,824 B1 | 12/2003 | Isaza et al. |
| 6,675,801 B2 | 1/2004 | Wallace et al. |
| 6,718,974 B1 | 4/2004 | Moberg |
| 6,725,447 B1 | 4/2004 | Gilman et al. |
| 6,739,337 B2 | 5/2004 | Isaza |
| 6,761,167 B1 | 7/2004 | Nadjafizadeh et al. |
| 6,761,168 B1 | 7/2004 | Nadjafizadeh et al. |
| 6,814,074 B1 | 11/2004 | Nadjafizadeh et al. |
| 6,866,040 B1 | 3/2005 | Bourdon |
| 6,960,854 B2 | 11/2005 | Nadjafizadeh et al. |
| 7,036,504 B2 | 5/2006 | Wallace et al. |
| 7,077,131 B2 | 7/2006 | Hansen |
| RE39,225 E | 8/2006 | Isaza et al. |
| 7,117,438 B2 | 10/2006 | Wallace et al. |
| 7,270,126 B2 | 9/2007 | Wallace et al. |
| 7,369,757 B2 | 5/2008 | Farbarik |
| 7,370,650 B2 | 5/2008 | Nadjafizadeh et al. |
| 7,428,902 B2 | 9/2008 | Du et al. |
| 7,460,959 B2 | 12/2008 | Jafari |
| 7,487,773 B2 | 2/2009 | Li |
| 7,654,802 B2 | 2/2010 | Crawford, Jr. et al. |
| 7,694,677 B2 | 4/2010 | Tang |
| 7,717,113 B2 | 5/2010 | Andrieux |
| D618,356 S | 6/2010 | Ross |
| 7,784,461 B2 | 8/2010 | Figueiredo et al. |
| 7,823,588 B2 | 11/2010 | Hansen |
| 7,855,716 B2 | 12/2010 | McCreary et al. |
| D632,796 S | 2/2011 | Ross et al. |
| D632,797 S | 2/2011 | Ross et al. |
| 7,891,354 B2 | 2/2011 | Farbarik |
| 7,893,560 B2 | 2/2011 | Carter |
| D638,852 S | 5/2011 | Skidmore et al. |
| 7,984,714 B2 | 7/2011 | Hausmann et al. |
| D643,535 S | 8/2011 | Ross et al. |
| 7,992,557 B2 | 8/2011 | Nadjafizadeh et al. |
| 8,001,967 B2 | 8/2011 | Wallace et al. |
| D645,158 S | 9/2011 | Sanchez et al. |
| 8,021,310 B2 | 9/2011 | Sanborn et al. |
| D649,157 S | 11/2011 | Skidmore et al. |
| D652,521 S | 1/2012 | Ross et al. |
| D652,936 S | 1/2012 | Ross et al. |
| D653,749 S | 2/2012 | Winter et al. |
| 8,113,062 B2 | 2/2012 | Graboi et al. |
| D655,405 S | 3/2012 | Winter et al. |
| D655,809 S | 3/2012 | Winter et al. |
| D656,237 S | 3/2012 | Sanchez et al. |
| 8,181,648 B2 | 5/2012 | Perine et al. |
| 8,210,173 B2 | 7/2012 | Vandine |
| 8,210,174 B2 | 7/2012 | Farbarik |
| 8,240,684 B2 | 8/2012 | Ross et al. |
| 8,267,085 B2 | 9/2012 | Jafari et al. |

(56) References Cited

U.S. PATENT DOCUMENTS

| | | |
|---|---|---|
| 8,272,379 B2 | 9/2012 | Jafari et al. |
| 8,272,380 B2 | 9/2012 | Jafari et al. |
| 8,302,600 B2 | 11/2012 | Andrieux et al. |
| 8,302,602 B2 | 11/2012 | Andrieux et al. |
| 8,312,879 B2 | 11/2012 | Choncholas et al. |
| 8,457,706 B2 | 6/2013 | Baker, Jr. |
| D692,556 S | 10/2013 | Winter |
| 8,567,399 B2 | 10/2013 | Wondka et al. |
| D693,001 S | 11/2013 | Winter |
| D701,601 S | 3/2014 | Winter |
| 8,792,949 B2 | 7/2014 | Baker, Jr. |
| D731,048 S | 6/2015 | Winter |
| D731,049 S | 6/2015 | Winter |
| D731,065 S | 6/2015 | Winter |
| D736,905 S | 8/2015 | Winter |
| D744,095 S | 11/2015 | Winter |
| 2003/0066528 A1* | 4/2003 | Hill ............ A61M 16/026 128/204.18 |
| 2005/0039748 A1 | 2/2005 | Andrieux |
| 2005/0139212 A1 | 6/2005 | Bourdon |
| 2006/0086357 A1* | 4/2006 | Soliman ........ A61M 16/0051 128/204.22 |
| 2007/0017515 A1 | 1/2007 | Wallace et al. |
| 2007/0077200 A1 | 4/2007 | Baker |
| 2007/0227537 A1 | 10/2007 | Bemister et al. |
| 2007/0272241 A1 | 11/2007 | Sanborn et al. |
| 2007/0284361 A1 | 12/2007 | Nadjafizadeh et al. |
| 2008/0053441 A1 | 3/2008 | Gottlib et al. |
| 2008/0060656 A1 | 3/2008 | Isaza |
| 2008/0072896 A1 | 3/2008 | Setzer et al. |
| 2008/0072902 A1 | 3/2008 | Setzer et al. |
| 2008/0078390 A1 | 4/2008 | Milne et al. |
| 2008/0083644 A1 | 4/2008 | Janbakhsh et al. |
| 2008/0092894 A1 | 4/2008 | Nicolazzi et al. |
| 2008/0097234 A1 | 4/2008 | Nicolazzi et al. |
| 2009/0165795 A1 | 7/2009 | Nadjafizadeh et al. |
| 2009/0171176 A1 | 7/2009 | Andersohn |
| 2009/0188499 A1 | 7/2009 | Chekal et al. |
| 2009/0205661 A1 | 8/2009 | Stephenson et al. |
| 2009/0205663 A1 | 8/2009 | Vandine et al. |
| 2009/0241952 A1 | 10/2009 | Nicolazzi et al. |
| 2009/0241953 A1 | 10/2009 | Vandine et al. |
| 2009/0241956 A1 | 10/2009 | Baker, Jr. et al. |
| 2009/0241957 A1 | 10/2009 | Baker, Jr. |
| 2009/0241958 A1 | 10/2009 | Baker, Jr. |
| 2009/0241962 A1 | 10/2009 | Jafari et al. |
| 2009/0247848 A1 | 10/2009 | Baker, Jr. |
| 2009/0247849 A1 | 10/2009 | McCutcheon et al. |
| 2009/0247853 A1 | 10/2009 | Debreczeny |
| 2009/0247891 A1 | 10/2009 | Wood |
| 2009/0287070 A1 | 11/2009 | Baker, Jr. |
| 2009/0301486 A1 | 12/2009 | Masic |
| 2009/0301487 A1 | 12/2009 | Masic |
| 2009/0301490 A1 | 12/2009 | Masic |
| 2009/0301491 A1 | 12/2009 | Masic et al. |
| 2010/0011307 A1 | 1/2010 | Desfossez et al. |
| 2010/0024820 A1 | 2/2010 | Bourdon |
| 2010/0051026 A1 | 3/2010 | Graboi |
| 2010/0051029 A1 | 3/2010 | Jafari et al. |
| 2010/0069761 A1 | 3/2010 | Karst et al. |
| 2010/0071689 A1 | 3/2010 | Thiessen |
| 2010/0071692 A1 | 3/2010 | Porges |
| 2010/0071695 A1 | 3/2010 | Thiessen |
| 2010/0071696 A1 | 3/2010 | Jafari |
| 2010/0071697 A1 | 3/2010 | Jafari et al. |
| 2010/0078017 A1 | 4/2010 | Andrieux et al. |
| 2010/0078026 A1 | 4/2010 | Andrieux et al. |
| 2010/0081119 A1 | 4/2010 | Jafari et al. |
| 2010/0081955 A1 | 4/2010 | Wood, Jr. et al. |
| 2010/0139660 A1 | 6/2010 | Adahan |
| 2010/0147303 A1 | 6/2010 | Jafari et al. |
| 2010/0186744 A1 | 7/2010 | Andrieux |
| 2010/0218765 A1 | 9/2010 | Jafari et al. |
| 2010/0218766 A1 | 9/2010 | Milne |
| 2010/0218767 A1 | 9/2010 | Jafari et al. |
| 2010/0236555 A1 | 9/2010 | Jafari et al. |
| 2010/0242961 A1 | 9/2010 | Mougel et al. |
| 2010/0249549 A1 | 9/2010 | Baker, Jr. et al. |
| 2010/0282259 A1 | 11/2010 | Figueiredo et al. |
| 2010/0288283 A1 | 11/2010 | Campbell et al. |
| 2010/0300446 A1 | 12/2010 | Nicolazzi et al. |
| 2011/0011400 A1 | 1/2011 | Gentner et al. |
| 2011/0023878 A1 | 2/2011 | Thiessen |
| 2011/0023879 A1 | 2/2011 | Vandine et al. |
| 2011/0023880 A1 | 2/2011 | Thiessen |
| 2011/0023881 A1 | 2/2011 | Thiessen |
| 2011/0029910 A1 | 2/2011 | Thiessen |
| 2011/0041849 A1 | 2/2011 | Chen et al. |
| 2011/0041850 A1 | 2/2011 | Vandine et al. |
| 2011/0126829 A1 | 6/2011 | Carter et al. |
| 2011/0126832 A1 | 6/2011 | Winter et al. |
| 2011/0126834 A1 | 6/2011 | Winter et al. |
| 2011/0126835 A1 | 6/2011 | Winter et al. |
| 2011/0126836 A1 | 6/2011 | Winter et al. |
| 2011/0126837 A1 | 6/2011 | Winter et al. |
| 2011/0128008 A1 | 6/2011 | Carter |
| 2011/0132361 A1 | 6/2011 | Sanchez |
| 2011/0132362 A1 | 6/2011 | Sanchez |
| 2011/0132364 A1 | 6/2011 | Ogilvie et al. |
| 2011/0132365 A1 | 6/2011 | Patel et al. |
| 2011/0132366 A1 | 6/2011 | Ogilvie et al. |
| 2011/0132367 A1 | 6/2011 | Patel |
| 2011/0132368 A1 | 6/2011 | Sanchez et al. |
| 2011/0132369 A1 | 6/2011 | Sanchez |
| 2011/0132371 A1 | 6/2011 | Sanchez et al. |
| 2011/0133936 A1 | 6/2011 | Sanchez et al. |
| 2011/0138308 A1 | 6/2011 | Palmer et al. |
| 2011/0138309 A1 | 6/2011 | Skidmore et al. |
| 2011/0138311 A1 | 6/2011 | Palmer |
| 2011/0138315 A1 | 6/2011 | Vandine et al. |
| 2011/0138323 A1 | 6/2011 | Skidmore et al. |
| 2011/0146681 A1 | 6/2011 | Jafari et al. |
| 2011/0146683 A1 | 6/2011 | Jafari et al. |
| 2011/0154241 A1 | 6/2011 | Skidmore et al. |
| 2011/0175728 A1 | 7/2011 | Baker, Jr. |
| 2011/0196251 A1 | 8/2011 | Jourdain et al. |
| 2011/0209702 A1 | 9/2011 | Vuong et al. |
| 2011/0209704 A1 | 9/2011 | Jafari et al. |
| 2011/0209707 A1 | 9/2011 | Terhark |
| 2011/0213215 A1 | 9/2011 | Doyle et al. |
| 2011/0230780 A1 | 9/2011 | Sanborn et al. |
| 2011/0249006 A1 | 10/2011 | Wallace et al. |
| 2011/0259330 A1 | 10/2011 | Jafari et al. |
| 2011/0259332 A1 | 10/2011 | Sanchez et al. |
| 2011/0259333 A1 | 10/2011 | Sanchez et al. |
| 2011/0265024 A1 | 10/2011 | Leone et al. |
| 2011/0271960 A1 | 11/2011 | Milne et al. |
| 2011/0273299 A1 | 11/2011 | Milne et al. |
| 2012/0000467 A1 | 1/2012 | Milne et al. |
| 2012/0000468 A1 | 1/2012 | Milne et al. |
| 2012/0000469 A1 | 1/2012 | Milne et al. |
| 2012/0000470 A1 | 1/2012 | Milne et al. |
| 2012/0029317 A1 | 2/2012 | Doyle et al. |
| 2012/0030611 A1 | 2/2012 | Skidmore |
| 2012/0060841 A1 | 3/2012 | Crawford, Jr. et al. |
| 2012/0071729 A1 | 3/2012 | Doyle et al. |
| 2012/0090611 A1 | 4/2012 | Graboi et al. |
| 2012/0096381 A1 | 4/2012 | Milne et al. |
| 2012/0133519 A1 | 5/2012 | Milne et al. |
| 2012/0136222 A1 | 5/2012 | Doyle et al. |
| 2012/0137249 A1 | 5/2012 | Milne et al. |
| 2012/0137250 A1 | 5/2012 | Milne et al. |
| 2012/0167885 A1 | 7/2012 | Masic et al. |
| 2012/0185792 A1 | 7/2012 | Kimm et al. |
| 2012/0197578 A1 | 8/2012 | Vig et al. |
| 2012/0197580 A1 | 8/2012 | Vij et al. |
| 2012/0211008 A1 | 8/2012 | Perine et al. |
| 2012/0216809 A1 | 8/2012 | Milne et al. |
| 2012/0216810 A1 | 8/2012 | Jafari et al. |
| 2012/0216811 A1 | 8/2012 | Kimm et al. |
| 2012/0226444 A1 | 9/2012 | Milne et al. |
| 2012/0247471 A1 | 10/2012 | Masic et al. |
| 2012/0272960 A1 | 11/2012 | Milne |
| 2012/0272961 A1 | 11/2012 | Masic et al. |

(56) References Cited

U.S. PATENT DOCUMENTS

| | | |
|---|---|---|
| 2012/0272962 A1 | 11/2012 | Doyle et al. |
| 2012/0277616 A1 | 11/2012 | Sanborn et al. |
| 2012/0279501 A1 | 11/2012 | Wallace et al. |
| 2012/0304995 A1 | 12/2012 | Kauc |
| 2012/0304997 A1 | 12/2012 | Jafari et al. |
| 2013/0000644 A1 | 1/2013 | Thiessen |
| 2013/0006133 A1 | 1/2013 | Doyle et al. |
| 2013/0006134 A1 | 1/2013 | Doyle et al. |
| 2013/0008443 A1 | 1/2013 | Thiessen |
| 2013/0025596 A1 | 1/2013 | Jafari et al. |
| 2013/0025597 A1 | 1/2013 | Doyle et al. |
| 2013/0032151 A1 | 2/2013 | Adahan |
| 2013/0042869 A1 | 2/2013 | Andrieux et al. |
| 2013/0047983 A1 | 2/2013 | Andrieux et al. |
| 2013/0047989 A1 | 2/2013 | Vandine et al. |
| 2013/0053717 A1 | 2/2013 | Vandine et al. |
| 2013/0074844 A1 | 3/2013 | Kimm et al. |
| 2013/0081536 A1 | 4/2013 | Crawford, Jr. et al. |
| 2013/0104896 A1 | 5/2013 | Kimm et al. |
| 2013/0146055 A1 | 6/2013 | Jafari et al. |
| 2013/0152923 A1 | 6/2013 | Andrieux et al. |
| 2013/0158370 A1 | 6/2013 | Doyle et al. |
| 2013/0159912 A1 | 6/2013 | Baker, Jr. |
| 2013/0167842 A1 | 7/2013 | Jafari et al. |
| 2013/0167843 A1 | 7/2013 | Kimm et al. |
| 2013/0186397 A1 | 7/2013 | Patel |
| 2013/0186400 A1 | 7/2013 | Jafari et al. |
| 2013/0186401 A1 | 7/2013 | Jafari et al. |
| 2013/0192599 A1 | 8/2013 | Nakai et al. |
| 2013/0220324 A1 | 8/2013 | Jafari et al. |
| 2013/0228172 A1 | 9/2013 | Young et al. |
| 2013/0233314 A1 | 9/2013 | Jafari et al. |
| 2013/0233319 A1 | 9/2013 | Winter et al. |
| 2013/0239038 A1 | 9/2013 | Skidmore et al. |
| 2013/0239967 A1 | 9/2013 | Jafari et al. |
| 2013/0255682 A1 | 10/2013 | Jafari et al. |
| 2013/0255685 A1 | 10/2013 | Jafari et al. |
| 2013/0255691 A1 | 10/2013 | Mansfield et al. |
| 2013/0276788 A1 | 10/2013 | Masic |
| 2013/0283197 A1 | 10/2013 | Skidmore |
| 2013/0284172 A1 | 10/2013 | Doyle et al. |
| 2013/0284173 A1 | 10/2013 | Masic et al. |
| 2013/0284177 A1 | 10/2013 | Li et al. |
| 2013/0327331 A1 | 12/2013 | Bourdon |
| 2013/0333697 A1 | 12/2013 | Carter et al. |
| 2013/0333703 A1 | 12/2013 | Wallace et al. |
| 2013/0338514 A1 | 12/2013 | Karst et al. |
| 2013/0345532 A1 | 12/2013 | Doyle et al. |
| 2014/0000606 A1 | 1/2014 | Doyle et al. |
| 2014/0012150 A1 | 1/2014 | Milne et al. |
| 2014/0034054 A1 | 2/2014 | Angelico et al. |
| 2014/0034056 A1 | 2/2014 | Leone et al. |
| 2014/0048071 A1 | 2/2014 | Milne et al. |
| 2014/0048072 A1 | 2/2014 | Angelico et al. |
| 2014/0121553 A1 | 5/2014 | Milne et al. |
| 2014/0123979 A1 | 5/2014 | Doyle et al. |
| 2014/0130798 A1 | 5/2014 | Milne et al. |
| 2014/0182590 A1 | 7/2014 | Platt et al. |
| 2014/0224250 A1 | 8/2014 | Sanchez et al. |
| 2014/0251328 A1 | 9/2014 | Graboi et al. |
| 2014/0261409 A1 | 9/2014 | Dong et al. |
| 2014/0261410 A1 | 9/2014 | Sanchez et al. |
| 2014/0261424 A1 | 9/2014 | Doyle et al. |
| 2014/0276176 A1 | 9/2014 | Winter |
| 2014/0290657 A1 | 10/2014 | Vandine et al. |
| 2014/0309507 A1 | 10/2014 | Baker, Jr. |
| 2014/0345616 A1 | 11/2014 | Masic |
| 2014/0360497 A1 | 12/2014 | Jafari et al. |
| 2014/0366879 A1 | 12/2014 | Kimm et al. |
| 2014/0373845 A1 | 12/2014 | Dong |
| 2015/0034082 A1 | 2/2015 | Kimm et al. |
| 2015/0045687 A1 | 2/2015 | Nakai et al. |
| 2015/0090258 A1 | 4/2015 | Milne et al. |
| 2015/0090264 A1 | 4/2015 | Dong |
| 2015/0107584 A1 | 4/2015 | Jafari et al. |
| 2015/0335839 A1 | 11/2015 | Mersmann et al. |
| 2016/0045694 A1 | 2/2016 | Esmaeil-zadeh-azar |
| 2016/0114115 A1 | 4/2016 | Glenn et al. |
| 2017/0072152 A1* | 3/2017 | Han .................. A61M 16/204 |

OTHER PUBLICATIONS

7200 Ventilatory System: Addendum/Errata. Nellcor Puritan Bennett, Part No. 4-023576-00, Rev. A, Apr. 1998, pp. 1-32.

800 Operator's and Technical Reference Manual. Series Ventilator System, Nellcor Puritan Bennett, Part No. 4-070088-00, Rev. L, Aug. 2010, pp. 1-476.

840 Operator's and Technical Reference Manual. Ventilator System, Nellcor Puritan Bennett, Part No. 4-075609-00, Rev. G, Oct. 2006, pp. 1-424.

Bunnell Incorporated, "Life Pulse High Frequency Ventilator In-Service Manual", relevant section: Chapter 7; p. 35 and Chapter 11; p. 59, Versin 01513-07.12, 103 pages.

* cited by examiner

ENDOTRACHEAL TUBE EXTUBATION DETECTION

CROSS-REFERENCE TO RELATED APPLICATION

This application claims the benefit of U.S. Provisional Application No. 62/324,108, filed Apr. 18, 2016, which is incorporated herein by reference in its entirety.

INTRODUCTION

Medical ventilator systems are used to provide ventilatory and supplemental oxygen support to patients. These ventilators typically comprise a source of pressurized oxygen which is fluidly connected to the patient through a conduit or tubing. As each patient may require a different ventilation strategy, modern ventilators can be customized for the particular needs of an individual patient. For example, several different ventilator modes or settings have been created to provide better ventilation for patients in various different scenarios, such as mandatory ventilation modes and spontaneous ventilation modes.

In some instances, ventilation is provided to patients through an endotracheal tube (ETT). In general, the ETT is inserted into the trachea of the patient to establish an airway between the patient and the rest the ventilator system. Most commonly, the ETT may be inserted through the mouth (orotracheal) or via surgical tracheotomy, however, other potential insertion techniques are possible (e.g., through the nasal passage, nasotracheal).

Endotracheal Tube Extubation Detection

This disclosure describes systems and methods for providing detection of extubation of an endotracheal tube (ETT). Further, this disclosure describes systems and methods for detecting and handling ETT extubation.

In one aspect, the technology relates to a method for detecting extubation of an endotracheal tube during ventilation. The method includes determining a first volume of breathing gas delivered to a patient during a first inspiratory period and determining a second volume of breathing gas delivered to a patient during a second inspiratory period. The method further includes determining a difference between the first volume and the second volume and comparing the determined value for the difference between the first volume and the second volume to a threshold. The method also includes, if the determined value for the difference is greater than the threshold, activating an alarm indicating extubation of the endotracheal tube.

In another aspect, the technology relates to a method for detecting extubation of an endotracheal tube during ventilation. The method includes measuring inspiratory pressure during a first inspiratory period having a first time duration and measuring inspiratory pressure during a second inspiratory period having a second time duration. The method also includes calculating a first integral over the first time duration of the inspiratory pressure measured during the first inspiratory period, and calculating a second integral over the second time duration of the inspiratory pressure measure during the second inspiratory period. In addition, the method includes comparing the first integral to the second integral to determine a difference between the first integral and the second integral, and if the difference between the first integral and the second integral is greater than a threshold, activating an alarm indicating extubation of the endotracheal tube.

In yet another aspect, the technology relates to a ventilator system. The ventilator system comprises a pressure generating system adapted to generate a flow of breathing gas; and a ventilation tubing system including a patient interface for connecting the pressure generating system to a patient, wherein the ventilation tubing system further includes an inspiratory limb, an expiratory limb, an endotracheal tube, and a wye connecting the inspiratory limb, the expiratory limb, and the endotracheal tube. The system also includes an inspiratory flow sensor coupled to at least one of the pressure generating system and the ventilation tubing system, an inspiratory pressure sensor coupled to the inspiratory limb, and an expiratory pressure sensor coupled to the expiratory limb. In addition, the system includes an interface for displaying operational data for the ventilator system and one or processors operatively coupled to at least the inspiratory pressure sensor and the expiratory sensor. The system further includes a memory operatively coupled to the one or more processors, wherein the memory includes instructions configured to perform a set of operations upon execution by the one or more processors. The set of operations includes determining a first volume of the breathing gas delivered to a patient during a first inspiratory period, and determining a second volume of breathing gas delivered to a patient during a second inspiratory period. The set of operations also includes determining a difference between the first volume and the second volume; comparing a value for the determined difference between the first volume and the second volume to a threshold; and if the determined value for the difference is greater than the threshold, activating an alarm in the interface indicating extubation of the endotracheal tube.

It is to be understood that both the foregoing general description and the following detailed description are exemplary and explanatory and are intended to provide further explanation of the invention as claimed.

BRIEF DESCRIPTION OF THE DRAWINGS

The patent or application file contains at least one drawing executed in color. Copies of this patent or patent application publication with color drawing(s) will be provided by the Office upon request and payment of the necessary fee. The following drawing figures, which form a part of this application, are illustrative of embodiments of systems and methods described below and are not meant to limit the scope of the invention in any manner, which scope shall be based on the claims.

DETAILED DESCRIPTION

Figure 1A:
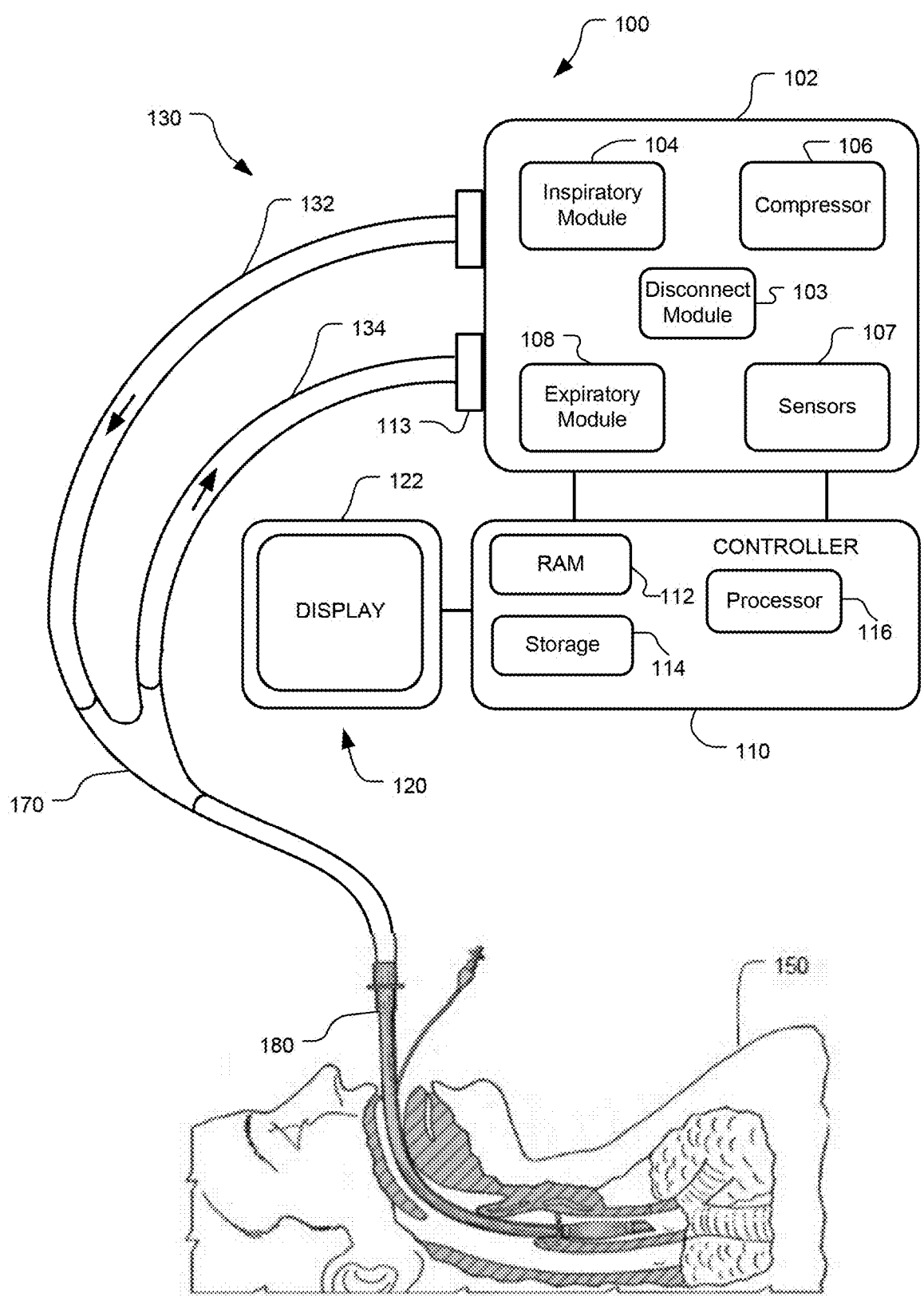
FIG. 1A illustrates an embodiment of a ventilator.

Although the techniques introduced above and discussed in detail below may be implemented for a variety of medical devices, the present disclosure will discuss the implementation of these techniques in the context of a medical ventilator for use in providing ventilation support to a human patient. A person of skill in the art will understand that the technology described in the context of a medical ventilator for human patients could be adapted for use with other systems such as ventilators for non-human patients and general gas transport systems.

Medical ventilators are used to provide a breathing gas to a patient who may otherwise be unable to breathe sufficiently. In modern medical facilities, pressurized air and oxygen sources are often available from wall outlets. Accordingly, ventilators may provide pressure regulating valves connected to centralized sources of pressurized air and pressurized oxygen. The regulating valves function to regulate flow so that respiratory gas having a desired concentration of oxygen is supplied to the patient at desired pressures and rates. Ventilators capable of operating independently of external sources of pressurized air are also available.

As each patient may require a different ventilation strategy, modern ventilators can be customized for the particular needs of an individual patient. For example, several different ventilator modes or settings have been created to provide better ventilation for patients in various different scenarios, such as mandatory ventilation modes and spontaneous ventilation modes. A particular type of mandatory ventilation referred to as assist/control (A/C) mode guarantees delivery of a minimum number of mandatory breaths based on a frequency (f) (or respiratory rate) set by the clinician. However, breaths in A/C mode can be patient-initiated (PIM) or ventilator-initiated (VIM). For a patient-initiated breath, inspiration is triggered at least in part based on the ventilator detecting a patient inspiratory effort.

In the event of malfunctions and/or system failures in ventilators, most ventilators sound an alarm and stop ventilation or potentially enter a passive state. For instance, if a component of the ventilator or the connecting circuitry becomes disconnected, an alarm is activated indicating that the patient is likely not receiving the desired or necessary amount of ventilation.

As discussed in further detail below, a ventilator provides breathing gas to a patient through a ventilation tubing system. The ventilation tubing system generally includes an inspiratory limb and an expiratory limb connected by a wye fitting. The wye fitting is further attached to a patient port connected to an ETT intubated into the patient. If any portion of the ventilation tubing system becomes disconnected, the patient may not receive the desired or necessary amount of breathing gas. Disconnects can occur at any one of the components in the ventilation tubing system. For instance, a disconnect may occur at (1) the inspiratory limb, (2) the expiratory limb, (3) the patient wye, or (4) between the ETT and the patient wye. A disconnect at any one of those positions can generally be detected utilizing conventional disconnect methods. When a disconnect is caused by extubation of the ETT, however, conventional disconnect detection methods cannot be used to detect a disconnect due to the extubation of an ETT. The extubation of the ETT is more difficult to detect, in part, because of the resistance of the ETT itself. Extubation detection becomes increasingly difficult for high-resistance ETTs, such as neo-natal ETTs.

Yet another difficulty in detecting any type of disconnection is that conventional disconnection methods often rely on a measurement of exhalation flow. That exhalation flow is generally measured using an exhalation flow sensor. The exhalation flow sensor, however, may be removed at times for cleaning or replacement. In addition, malfunctions in the exhalation flow sensor may also render conventional disconnection detection methods inoperable. Thus, when the exhalation flow sensor is removed or malfunctioning, the conventional disconnection detection methods are rendered inoperable. In either of those conditions, being able to detect disconnects is still desired. Indeed, in many ventilators, breath delivery continues even when the exhalation flow sensor is absent or malfunctioning.

Embodiments of the present technology provide methods and systems that enable detection of a disconnect caused by extubation of an ETT and also enable detection of disconnects without the use of an exhalation flow sensor. As an example, the present technology allows for using measurements or values such as inspiratory pressure, expiratory pressure, inspiratory volume, and time duration readings for detecting extubation of an ETT. In addition, the present technology is also able to detect disconnects without the use of a proximal flow sensor, or can be used to augment disconnect detection in embodiments utilizing a proximal flow sensor.

Figure 1B:
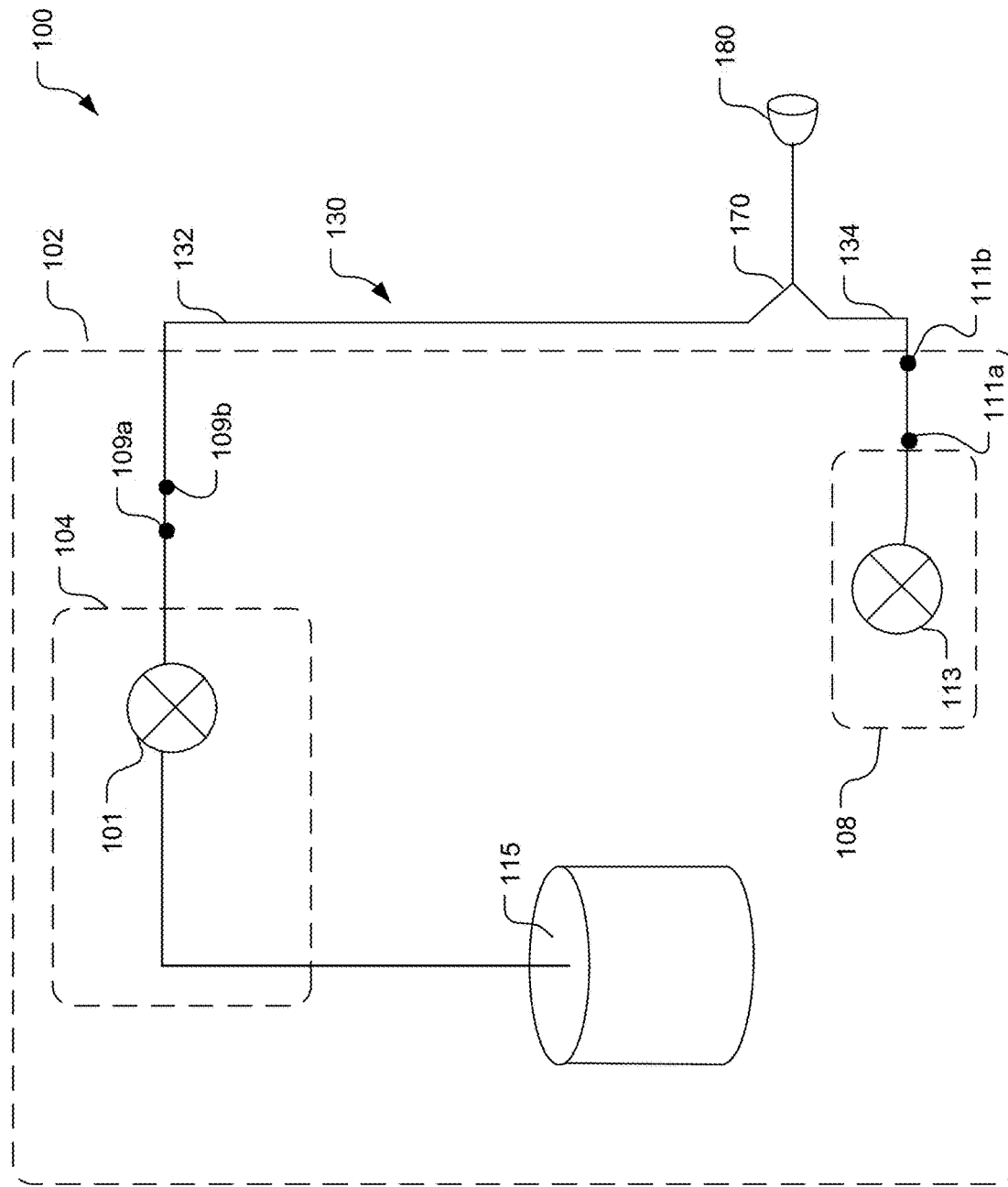
FIG. 1B illustrates an embodiment of the ventilator shown in FIG. 1A.

FIGS. 1A and 1B are diagrams illustrating an embodiment of an exemplary ventilator 100. The exemplary ventilator 100 illustrated in FIG. 1A is connected to a human patient 150. Ventilator 100 includes a pneumatic system 102 (also referred to as a pressure generating system 102) for circulating breathing gases to and from patient 150 via the ventilation tubing system 130, which couples the patient 150 to the pneumatic system 102 via an invasive (e.g., endotracheal tube, as shown) or a non-invasive (e.g., nasal mask) patient interface 180. The ETT may be a neo-natal ETT having a high resistance. In other examples, the ETT has a resistance in the range of 13.8 $H_2O$/L/sec at a flow of 0.167 L/sec to 0.7 $H_2O$/L/sec at a flow of 0.167 L/sec. The pneumatic system 102 delivers ventilation to the patient 150 according to predetermined or selected modes (spontaneous, assist, mandatory, etc.) and breath types (pressure control, pressure support, pressure assist, volume control, volume support, volume-controlled-pressure-targeted, etc.).

Ventilation tubing system 130 (or patient circuit 130) may be a two-limb (shown) or a one-limb circuit for carrying gases to and from the patient 150. In a two-limb embodiment, a fitting, typically referred to as a "wye-fitting" 170, may be provided to couple the patient interface 180 (shown as an endotracheal tube in FIG. 1A and as a nasal mask in FIG. 1B) to an inspiratory limb 132 and an exhalation limb 134 of the ventilation tubing system 130.

Pneumatic system 102 may be configured in a variety of ways. In the present example, pneumatic system 102 includes an exhalation module 108 coupled with the exhalation limb 134 and an inspiratory module 104 coupled with the inspiratory limb 132. Compressor 106, accumulator 115 (as illustrated in FIG. 1B) and/or other source(s) of pressurized gases (e.g., air, oxygen, and/or helium) is coupled with inspiratory module 104 and the exhalation module 108 to provide a gas source for ventilatory support via inspiratory limb 132.

The inspiratory module 104 is configured to deliver gases to the patient 150 and/or through the inspiratory limb 132 according to prescribed ventilatory settings. The inspiratory module 104 is associated with and/or controls an inspiratory delivery valve 101 for controlling gas delivery to the patient 150 and/or gas delivery through the inspiratory limb 132 as illustrated in FIG. 1B. In some embodiments, inspiratory module 104 is configured to provide ventilation according to various ventilator modes, such as mandatory and assist modes.

The exhalation module 108 is configured to release gases from the patient's lungs and/or exhalation circuit according to prescribed ventilatory settings. Accordingly, the exhalation module 108 also controls gas delivery through the inspiratory limb 132 and the exhalation limb 134. The exhalation module 108 controls an exhalation valve 113 which regulates the flow of gases from the patient's lungs and/or exhalation circuit according to prescribed ventilatory settings.

The ventilator 100 also includes a plurality of sensors 107 communicatively coupled to ventilator 100. The sensors 107 may be located in the pneumatic system 102, ventilation tubing system 130, and/or on the patient 150. The embodiment of FIG. 1A illustrates a plurality of sensors 107 in pneumatic system 102.

Sensors 107 may communicate with various components of ventilator 100, e.g., pneumatic system 102, other sensors 107, exhalation module 108, inspiratory module 104, processor 116, controller 110, and any other suitable components and/or modules. In one embodiment, sensors 107 generate output and send this output to pneumatic system 102, other sensors 107, exhalation module 108, inspiratory module 104, processor 116, controller 110, and any other suitable components and/or modules.

Sensors 107 may employ any suitable sensory or derivative technique for monitoring one or more patient parameters or ventilator parameters associated with the ventilation of a patient 150. Sensors 107 may detect changes in patient parameters indicative of patient inspiratory or exhalation triggering effort, for example. Sensors 107 may be placed in any suitable location, e.g., within the ventilatory circuitry or other devices communicatively coupled to the ventilator 100. Further, sensors 107 may be placed in any suitable internal location, such as, within the ventilatory circuitry or within components or modules of ventilator 100. For example, sensors 107 may be coupled to the inspiratory and/or exhalation modules 104, 108 for detecting changes in, for example, inspiratory flow, inspiratory pressure, expiratory pressure, and expiratory flow. In other examples, sensors 107 may be affixed to the ventilatory tubing or may be embedded in the tubing itself. According to some embodiments, sensors 107 may be provided at or near the lungs (or diaphragm) for detecting a pressure in the lungs. Sensors 107 may also include a proximal flow sensor. Additionally or alternatively, sensors 107 may be affixed or embedded in or near wye-fitting 170 and/or patient interface 180. The sensors may include one or more expiratory sensors for measuring the pressure on an expiratory portion of the patient circuit 130. The expiratory sensors may include a pressure sensor that may be affixed in such a way to measure the pressure on the expiratory limb 134. For instance, the expiratory sensor for measuring pressure may be affixed on or near the exhalation valve 113. The sensors may also include inspiratory sensors for measuring the pressure on an inspiratory portion of the patient circuit 130. For instance, the pressure in the inspiratory limb 132 may be measured by an inspiratory sensor. Any sensory device useful for monitoring changes in measurable parameters during ventilatory treatment may be employed in accordance with embodiments described herein.

For example, in some embodiments, the one or more sensors 107 of the ventilator 100 include an inspiratory flow sensor 109a and an exhalation flow sensor 111a as illustrated in FIG. 1B. In one embodiment, the inspiratory flow sensor 109a is located in the inspiratory limb 132 and is controlled by the inspiratory module 104. However, the inspiratory flow sensor 109a may be located in any suitable position for monitoring inspiratory flow and may be monitored by any suitable ventilator component, such as a pressure generating system 102. In one embodiment, the exhalation flow sensor 111 is located in the exhalation limb 134 and is monitored by the exhalation module 108. However, the exhalation flow sensor 111 may be located in any suitable position for monitoring exhalation flow and may be monitored by any suitable ventilator component, such as a pressure generating system 102.

Further, in some embodiments, the one or more sensors 107 of the ventilator 100 also include an inspiratory pressure sensor 109b and/or an expiratory pressure sensor 111b as illustrated in FIG. 1B. In one embodiment, the inspiratory pressure sensor 109b is located in the inspiratory limb 132 and is controlled by the inspiratory module 104. However, the inspiratory pressure sensor 109b may be located in any suitable position for monitoring inspiratory pressure and may be monitored by any suitable ventilator component, such as a pressure generating system 102. In one embodiment, the expiratory pressure sensor 111b is located in the exhalation limb 134 and is monitored by the exhalation module 108. However, the expiratory pressure sensor 111b may be located in any suitable position for monitoring expiratory pressure and may be monitored by any suitable ventilator component, such as a pressure generating system 102.

As should be appreciated, with reference to the Equation of Motion, ventilatory parameters are highly interrelated and, according to embodiments, may be either directly or indirectly monitored. That is, parameters may be directly monitored by one or more sensors 107, as described above, or may be indirectly monitored or estimated by derivation according to the Equation of Motion or other known relationships. For example, in some embodiments, inspiration flow is derived from measured inspiration pressure and vice versa. In another example, exhalation pressure is derived from exhalation flow and vice versa.

The pneumatic system 102 may include a variety of other components, including mixing modules, valves, tubing, accumulators 115, filters, etc. For example, FIG. 1B illustrates the use of an accumulator 115.

In one embodiment, as illustrated by FIG. 1A, the operator interface 120 of the ventilator 100 includes a display 122 communicatively coupled to ventilator 100. Display 122 provides various input screens, for receiving clinician input, and various display screens, for presenting useful information to the clinician. In one embodiment, the display 122 is configured to include a graphical user interface (GUI). The GUI may be an interactive display, e.g., a touch-sensitive screen or otherwise, and may provide various windows and elements for receiving input and interface command operations. Alternatively, other suitable means of communication with the ventilator 100 may be provided, for instance by a wheel, keyboard, mouse, or other suitable interactive device. Thus, operator interface 120 may accept commands and input through display 122.

Display 122 may also provide useful information in the form of various ventilatory data regarding the physical condition of a patient 150. The useful information may be derived by the ventilator 100, based on data collected by a processor 116, and the useful information may be displayed to the clinician in the form of graphs, wave representations, pie graphs, text, or other suitable forms of graphic display. For example, patient data may be displayed on the GUI and/or display 122. Additionally or alternatively, patient data may be communicated to a remote monitoring system coupled via any suitable means to the ventilator 100. In some embodiments, the display 122 may also display alarms associated with extubation of an ETT 180 or other disconnects in the patient circuit 130.

The pneumatic system 102 may also include a disconnect module 103. In some embodiments, the disconnect module 103 is in communication with the inspiratory module 104, the expiratory module 108, the sensors 107, and the controller 110. For example, the disconnect module 103 includes an interface to convert the raw signals received from the sensors 107 into data capable of being read and processed to determine if a disconnect, such as an extubation of an ETT, has occurred. The disconnect module 103, in cooperation with the controller 110, includes instructions that when executed by the processor 116, utilize the data from the sensors 107 to determine if a disconnect has occurred. For example, the instructions may be for performing the methods described herein. Upon detecting a disconnect, the disconnect module 103 transmits an indication causing the interface 120 to activate an alarm indicating a disconnect has occurred.

Controller 110 is operatively coupled with pneumatic system 102, signal measurement and acquisition systems, and an operator interface 120 that may enable an operator to interact with the ventilator 100 (e.g., change ventilator settings, select operational modes, view monitored parameters, etc.).

In some embodiments, controller 110 includes memory 112, one or more processors 116, storage 114, and/or other components of the type commonly found in command and control computing devices, as illustrated in FIG. 1A. In alternative embodiments, the controller 110 is separate component from the operator interface 120 and pneumatic system 102. In other embodiments, the controller 110 is located in other components of the ventilator 100, such as in the pressure generating system 102 (also known as the pneumatic system 102).

The memory 112 includes non-transitory, computer-readable storage media that stores software that is executed by the processor 116 and which controls the operation of the ventilator 100. In an embodiment, the memory 112 includes one or more solid-state storage devices such as flash memory chips. In an alternative embodiment, the memory 112 may be mass storage connected to the processor 116 through a mass storage controller (not shown) and a communications bus (not shown). Although the description of computer-readable media contained herein refers to a solid-state storage, it should be appreciated by those skilled in the art that computer-readable storage media can be any available media that can be accessed by the processor 116. That is, computer-readable storage media includes non-transitory, volatile and non-volatile, removable and non-removable media implemented in any method or technology for storage of information such as computer-readable instructions, data structures, program modules or other data. For example, computer-readable storage media includes RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information and which can be accessed by the computer.

Additionally, controller 110 determines if the ventilator 100 is in an inspiratory phase (delivering inspiration) or an expiratory phase (delivering exhalation) of breath during ventilation based on the mandatory mode of ventilation after a malfunction is determined. The ventilator 100 delivers inspiration and exhalation automatically based on the set frequency or respiratory rate. Accordingly, the ventilator 100 determines the inspiration and exhalation phases. In embodiments where the ventilator 100 operates in an A/C mode, the patient may initiate or trigger the breaths in a patient-initiated mode (PIM) or the ventilator may initiate or trigger the breaths in a ventilator-initiated mode (VIM). If the controller 110 determines that the ventilator 100 is in the inspiration phase of the breath, the pressure delivered to the patient 150 is a set inspiration pressure. In some embodiments, if the controller 110 determines that the ventilator 100 is in the exhalation phase of the breath, the pressure delivered to the patient 150 is a set positive end-expiratory pressure (PEEP).

Figure 2A:
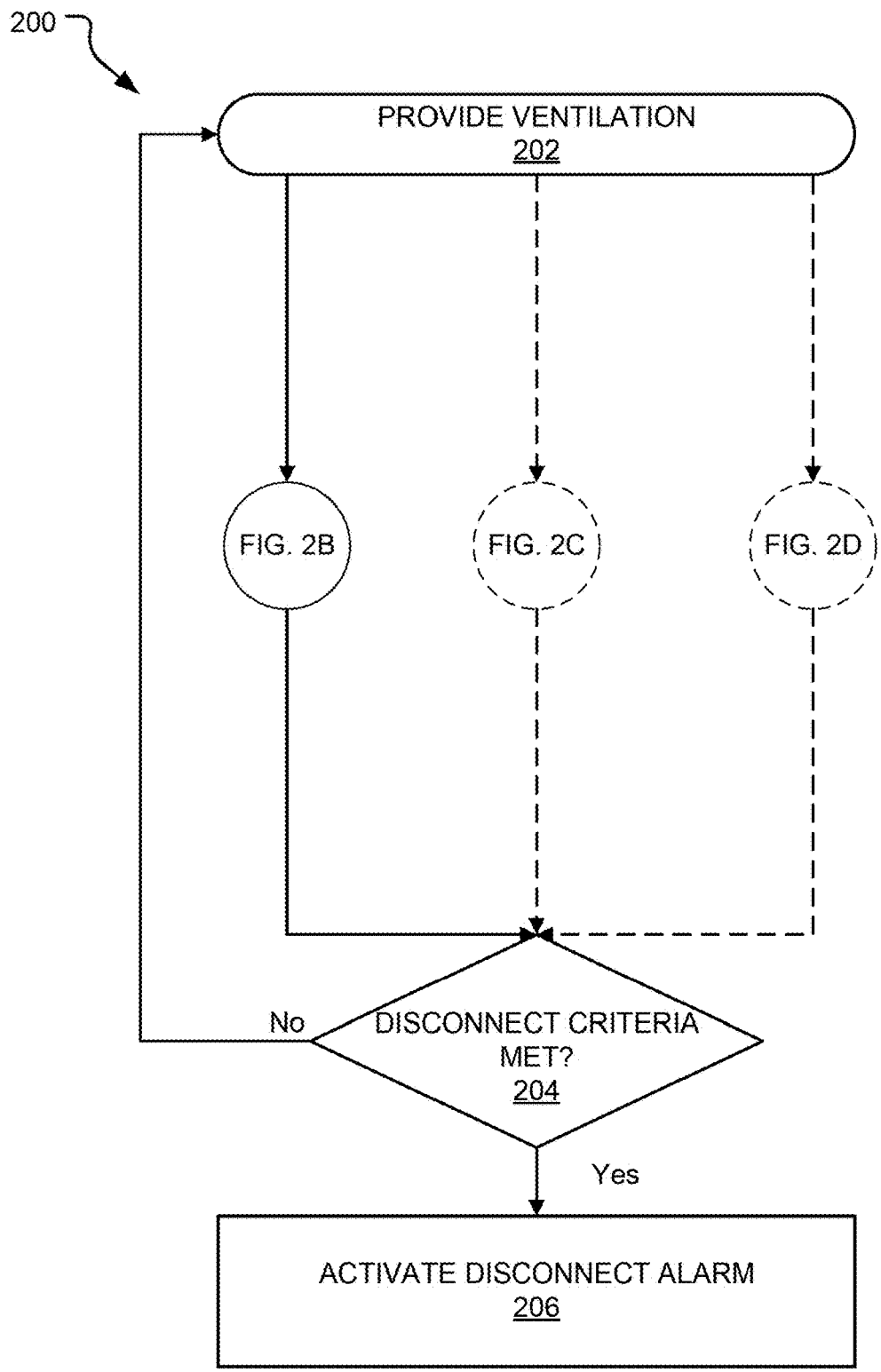
FIG. 2A illustrates an embodiment of a method for detecting ETT extubation.
Figure 2B:
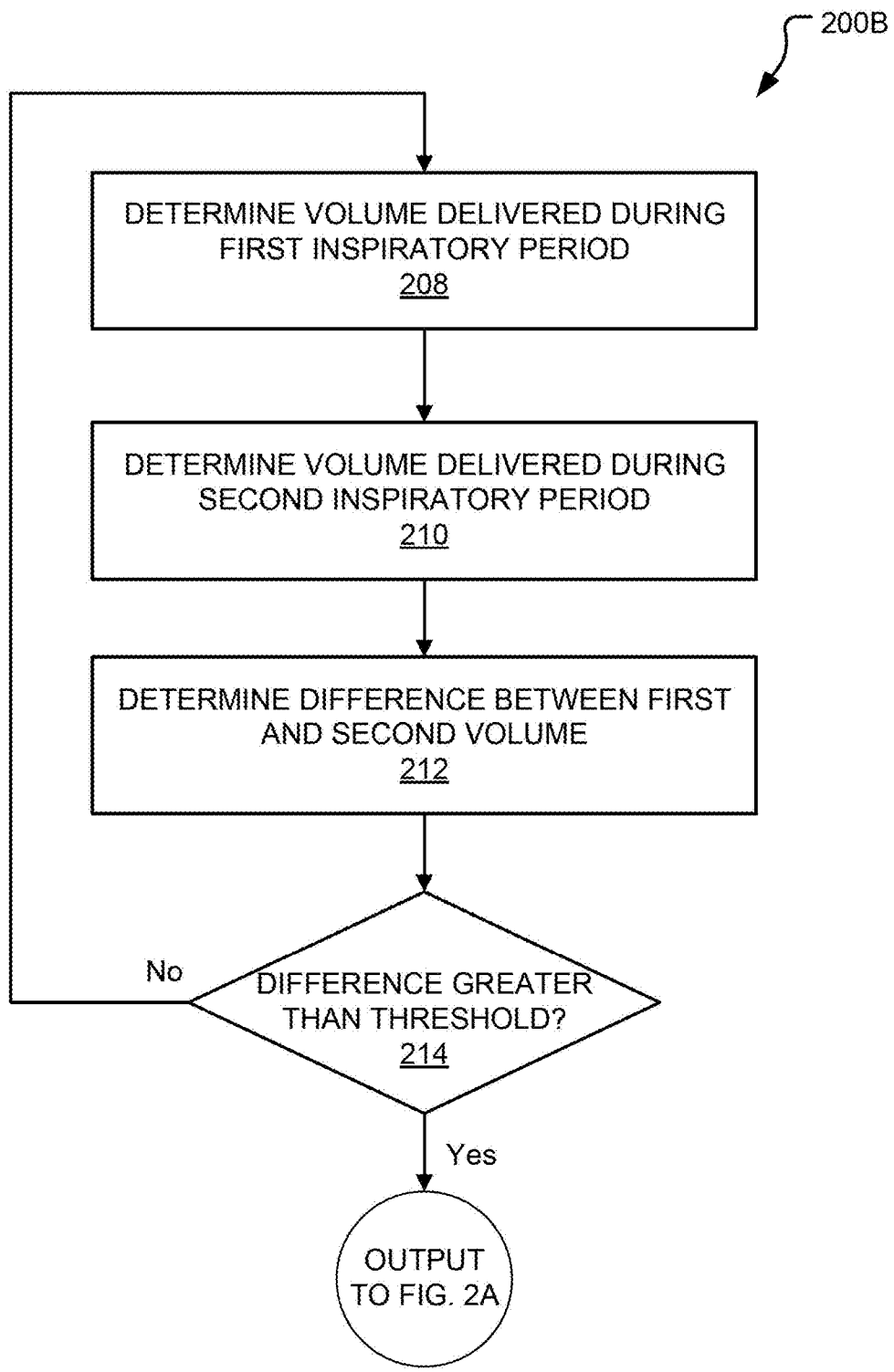
FIG. 2B illustrates an embodiment of a method for detecting ETT extubation parameters in conjunction with the method illustrated in FIG. 2A.
Figure 2C:
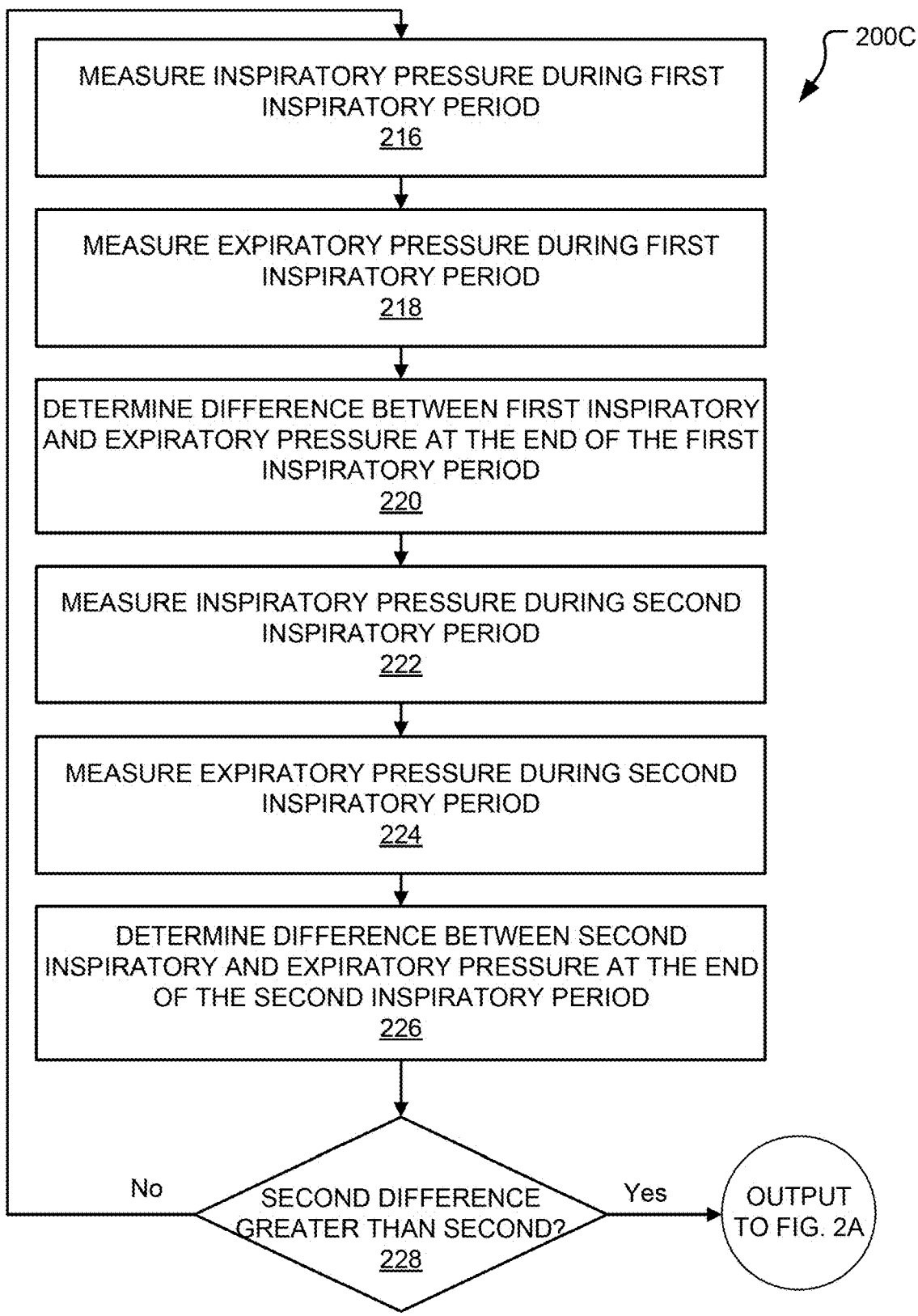
FIG. 2C illustrates an embodiment of a method for detecting ETT extubation parameters in conjunction with the method illustrated in FIG. 2A.
Figure 2D:
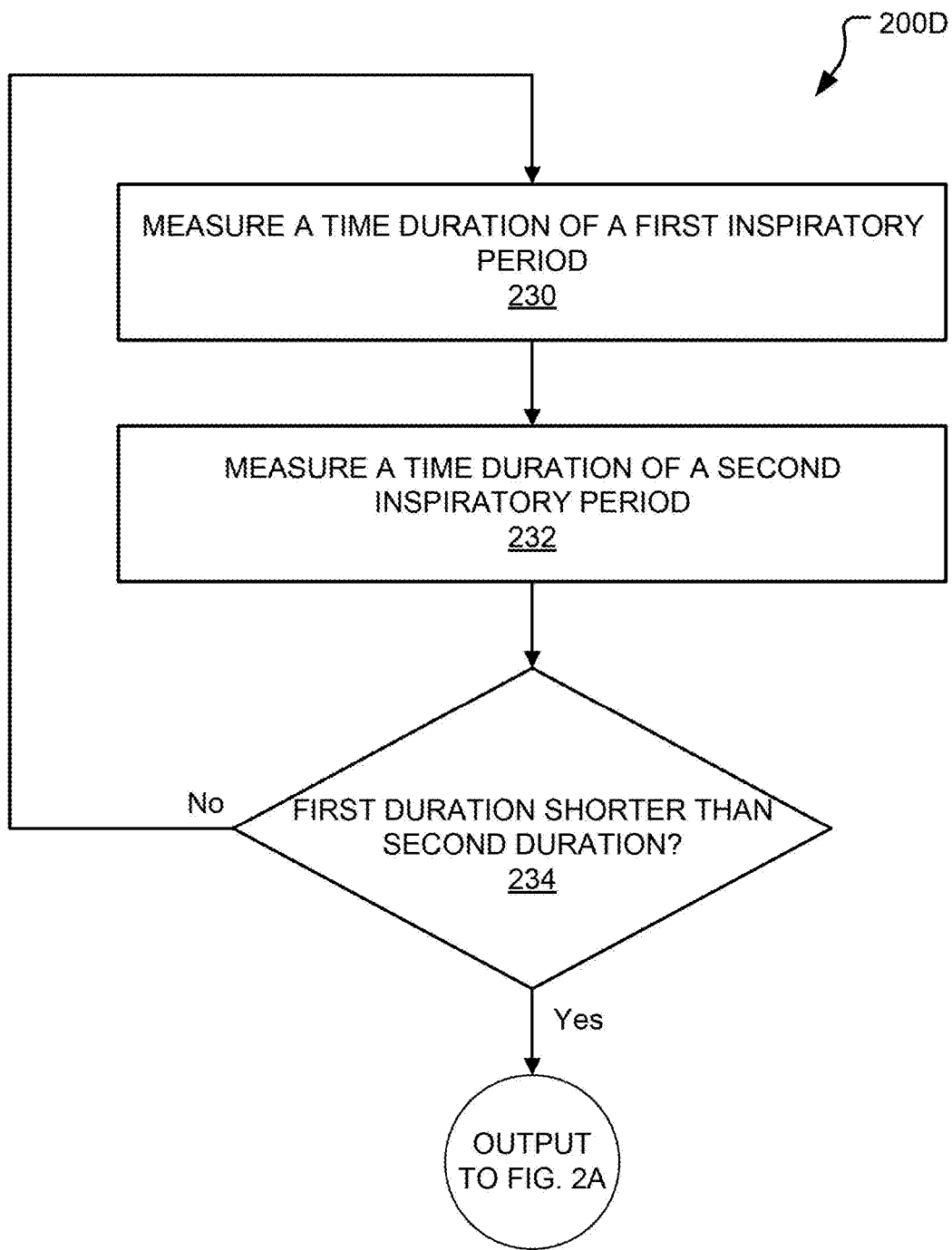
FIG. 2D illustrates an embodiment of a method for detecting ETT extubation parameters in conjunction with the method illustrated in FIG. 2A.

FIG. 2A illustrates an embodiment of a method 200 for ventilating a patient with a ventilator. Further, method 200 detects when a disconnect, such as extubation of an ETT, has occurred. Method 200 begins at the start of ventilation by providing ventilation at operation 202. During ventilation of a patient, disconnect detection operations are executed, as shown in FIGS. 2B-2D and described below. Each of the sub-methods shown in FIGS. 2B-2D monitor ventilator parameters and determine if those parameters are indicative of a disconnect. At operation 204, a determination is then made is a set of criteria is satisfied indicating a disconnect has occurred. The disconnect criteria may vary depending on the particular example. For instance, the following table (Table 1) indicates example criteria. In some examples, only one or two of the criterion highlighted below is utilized to determine if the disconnect criteria is met in operation 204.

TABLE 1

Disconnect Criteria

| Criterion Reference No. | Criterion Description | Related Equation | Related FIG. |
|---|---|---|---|
| 1 | The inspiratory volume increase in the current inspiratory period compared to the inspiratory volume of a previous inspiratory period is greater than or equal to a threshold | $\dfrac{V_{insp}(j) - V_{insp}(j-1)}{V_{insp}(j-1)} \geq \alpha$ | 2B |
| 2 | The pressure difference at the end of the current inspiration period between the inspiratory sensor pressure measurement and the expiratory sensor pressure measurement is greater than or equal to the pressure difference at the end of the previous inspiration | $P_{insp}(j) - P_{exp}(j) \geq P_{insp}(j-1) - P_{exp}(j-1)$ | 2C |
| 3 | A time duration for a current inspiratory period is greater than or equal to the time duration of the previous inspiratory period | $T_{insp}(j) \geq T_{insp}(j-1)$ | 2D |

In the above Table 1, the variables are defined as follows:

$V_{insp}$ = an inspiratory volume;

$\alpha$ = a threshold;

$P_{insp}$ = an inspiratory sensor pressure measurement;

$P_{exp}$ = an expiratory sensor pressure measurement;

$T_{insp}$ = a time duration for an inspiratory period; and j = an index value indicating a particular inspiratory period.

In embodiments where pressure-controlled ventilation is being provided, the disconnect criteria may include Criterion Reference Nos. 1 and 2, but not 3. In embodiments where pressure-support ventilation is being provided, all three criterion may be included in the disconnect criteria.

If the disconnect criteria for the particular embodiment is determined to be satisfied at operation 204, a disconnect alarm is activated at operation 206. The disconnect alarm may also indicate whether the extubation is a full extubation or a partial extubation, based on factors further discussed below. If, however, the disconnect criteria for the particular embodiment is not satisfied, ventilation continues to be provided at operation 202 and the method 200 repeats itself. The method 200 continues to run in a loop until the disconnect criteria is satisfied, or ventilation is otherwise discontinued, such as by a medical provider.

Sub-methods for detecting processing parameters involved with each criteria are depicted in FIGS. 2B-2D. FIG. 2B depicts a sub-method 200B for detecting and processing parameters associated with Criterion Reference No. 1. At operation 208, an inspiratory volume of breathing gas delivered to during a first inspiratory period is determined. The volume of breathing gas may be determined by measuring the inspiratory flow ($Q_{insp}$) during the first inspiratory period, and then taking the integral of the inspiratory flow over the time duration of the first inspiratory period. The flow may be measured by the inspiratory flow sensor, as discussed above. The following equation may be used to determine the volume of breathing gas delivered:

$$V_{insp} = \int_{t_S}^{t_E} Q_{insp}(t) \quad (1)$$

where $Q_{insp}(t)$ is the inspiratory flow at a time t, $t_S$ is the start time of the inspiratory period, and $t_E$ is the end time of the inspiratory period. At operation 210, a volume of breathing gas delivered to the patient during a second inspiratory period is determined. The inspiratory volume of breathing gas for the second period can be determined using Equation 1. At operation 212, the inspiratory volume for the first inspiratory period is then compared to the inspiratory volume for the second inspiratory period to determine a difference between the first inspiratory volume and the second inspiratory volume. In some embodiments, the second inspiratory period is the current inspiratory period during ventilation. In such an embodiment, the two inspiratory volumes being compared are the inspiratory volume of the current inspiratory period the inspiratory volume of the previous inspiratory period.

At operation 214, a determination is made as to whether the difference determined in operation 212 is greater than a threshold ($\alpha$). One example of a threshold is 0.3. Other threshold values are also contemplated ranging from 0.2-0.7. The following equation may be used in the determination operation 214:

$$\frac{V_{insp}(j) - V_{insp}(j-1)}{V_{insp}(j-1)} \geq \alpha \quad (2)$$

where $V_{insp}(j)$ is the inspiratory volume of the second inspiratory period and $V_{insp}(j-1)$ is the inspiratory volume for the first inspiratory period. As can be seen from Equation 2, the difference may be normalized by dividing the difference by $V_{insp}(j-1)$. In such an example, the threshold can be unitless. If the difference is greater than or equal to the threshold, that determination is used in operation 204 (FIG. 2A) to determine whether the disconnect criteria is satisfied. If the difference is less than the threshold, the method 200B returns to operation 208 where the method 200B repeats itself.

In some embodiments the threshold (a) may be predetermined or based on other ventilator properties. Multiple thresholds may also be used, where a first threshold indicates partial extubation and a second threshold indicates full extubation. For instance, when the difference determined in operation 212 is greater than or equal to a first threshold ($\alpha_1$), but less than a second threshold ($\alpha_2$), a partial extubation is identified. When the difference determined in operation 212 is greater than or equal to the second threshold ($\alpha_2$), a full extubation is identified. As an example, a first threshold may be 0.3 and a second threshold may be 0.6. Other thresholds are also contemplated. For example, the first threshold may be from 0.2-0.5 and the second threshold may be from 0.5-0.8.

FIG. 2C depicts a sub-method 200C for detecting and processing parameters associated with Criterion Reference No. 2. At operation 216, a pressure at an inspiratory sensor is measured at the end of a first inspiratory period. At operation 218, a pressure at an expiratory sensor is also measured at the end of the first inspiratory period. A difference between the inspiratory sensor pressure measurement and the expiratory sensor pressure measurement at the end of the first inspiratory period is determined at operation 220. Similar pressure measurements and determinations are then made for a second inspiratory period. For instance, at operation 222 an inspiratory sensor pressure measurement is measured at the end of the second inspiratory period. At operation 224, an expiratory sensor pressure measurement is measured at the end of the second inspiratory period. A difference between the inspiratory sensor pressure measurement and expiratory sensor pressure measurement at the end of the second inspiratory period is determined at operation 226. At operation 228, a determination is made as to whether the difference determined at operation 226 is greater than the difference determined at operation 220. If the difference determined at operation 226 is greater than or equal to the difference determined at operation 220, that determination is used in operation 204 (FIG. 2A) to determine whether the disconnect criteria is satisfied. If difference determined at operation 226 is less than the difference determined at operation 220, the method 200C returns to operation 216 where the method 200C repeats itself. The following equations may be utilized in performing sub-method 200C:

$$dP(j) = P_{insp.end}(j) - P_{exp.end}(j) \quad (3)$$

$$dP(j-1) = P_{insp.end}(j-1) - P_{exp.end}(j-1) \quad (4)$$

$$dP(j) \geq dP(j-1) \quad (5)$$

where $P_{insp.end}$ is the inspiratory sensor pressure measured at the end of an inspiratory period, and $P_{exp.end}$ is the expiratory sensor pressure measured at the end of an inspiratory period.

FIG. 2D depicts a sub-method 200D for detecting and processing parameters associated with Criterion Reference No. 3. At operation 230, a time duration of a first inspiratory period is measured, and at operation 232 a time duration of a second inspiratory period is measured. At operation 234, a determination is made as to whether the time duration for the first inspiratory period is shorter than the second time duration. If the time duration for the first inspiratory period is shorter than the second time duration, the determination is used in operation 204 (FIG. 2A) to determine whether the disconnect criteria is satisfied. If difference determined at operation 226 is less than the difference determined at operation 220, the method 200C returns to operation 216 where the method 200C repeats itself.

In embodiments where all three criterion are utilized in the disconnect criteria used in operation 204, the following pseudo-code may be implemented:

```
during inspiration phase
{
    V_insp = ∫_tS^tE Q_insp(t)
    dP(j) = P_insp.end(j) - P_exp.end(j)
}
at start of expiration phase
{
    if:

(V_insp(j) - V_insp(j - 1)) / V_insp(j - 1) ≥ α;

dP(j) ≥ dP(j - 1); and
        T_insp(j) ≥ T_insp(j - 1);
    then:
        activate disconnect alarm;
    else:
        continue ventilation
}
```

The disconnect criteria have been derived and determined through analysis of simulated ventilation scenarios, some of which are discussed below with reference to FIGS. 4-7. The disconnect criterion are also supported through an analysis of an equation of motion:

$$P_{vent} - P_{mus} = Q_{lung} \times R_{rs} + V_{lung} \times E_{rs} \quad (6)$$

where:
$P_{vent}$=pressure delivered by the ventilator;
$P_{mus}$=patient's muscle effort;
$Q_{lung}$=flow delivered to the patient's lung;
$R_{rs}$=respiratory system resistance;
$V_{lung}$=volume delivered to the patient's lung; and
$E_{rs}$=respiratory system elastance.

When an ETT is extubated, the respiratory system elastance decreases and the patient's muscle effort reduces to zero. Thus, Equation 6 becomes:

$$P_{vent} = Q_{lung} \times R_{rs} + V_{lung} \times E_{rs} \quad (7)$$

Based on Equation 7 and a reduced respiratory system elastance, a higher $Q_{lung}$ and/or a higher $V_{lung}$ are demanded to meet the required pressure $P_{vent}$.

Figure 3:
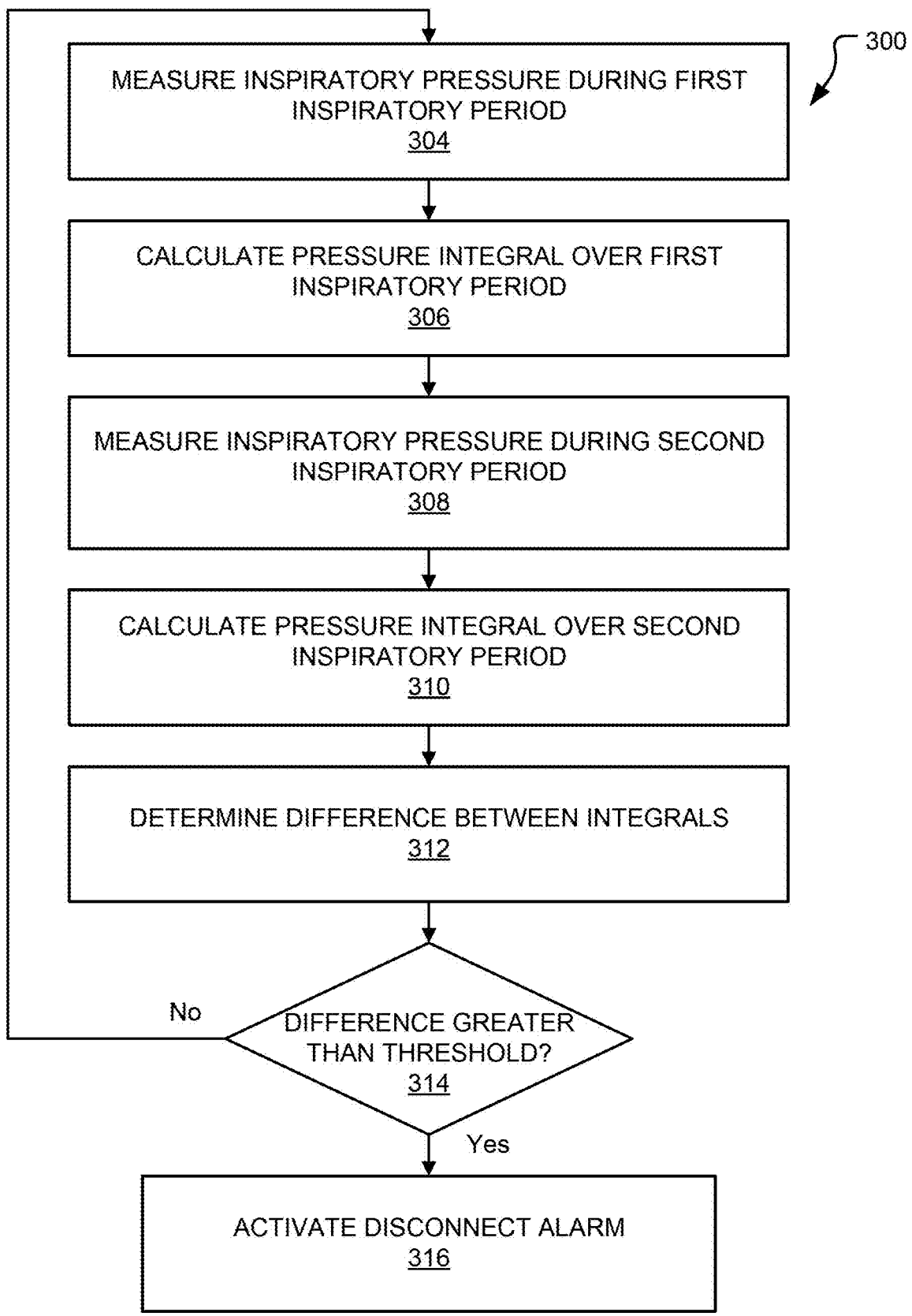
FIG. 3 illustrates another embodiment of a method for detecting ETT extubation.

FIG. 3 illustrates another embodiment of a method 300 for detecting ETT extubation. In general, method 300 is suitable for detecting a disconnect during volume-controlled ventilation or volume-support ventilation. Method 300 begins at the start of ventilation and continues during ventilation. At operation 304, an inspiratory sensor pressure is measured during a first inspiratory period. At operation 306, an integral is calculated for the inspiratory sensor pressure over the first inspiratory period. An inspiratory sensor pressure for a second inspiratory period is then measured at operation 308. At operation 310, an integral is calculated for the inspiratory sensor pressure over the second inspiratory period. A difference between the two integrals is then determined at operation 312. At operation 314, a determination is made as to whether the difference determined in operation 312 is greater than a threshold ($\beta$). If the difference determined in operation 312 is greater than or equal to a threshold ($\beta$), a disconnect alarm is activated. If, however, the difference determined in operation 312 is less than a threshold ($\beta$), the method 300 returns to operation 304 where the method 300 repeats itself. An example of threshold ($\beta$) is 0.5, and other thresholds, such as thresholds between 0.3-0.8 are also contemplated. Multiple thresholds may also be used to determine partial or full extubation. For instance, if the difference determined in operation 312 is greater than or equal to a first threshold ($\beta_1$), but less than a second threshold ($\beta_2$), an disconnect alarm is activated that indicates a partial extubation. If the difference determined in operation 312 is greater than or equal to the second threshold ($\beta_2$), a disconnect alarm is activated that indicates a full extubation. The following pseudo code may be implemented to perform at least a portion of method 300:

During inspiration phase:
{
   $W_{insp}(j) = \int P_{insp}$ ;
}
At start of expiration phase:
{
  if:
$$\frac{W_{insp}(j-1) - W_{insp}(j)}{W_{insp}(j-1)} \geq \beta$$
  then:
    activate disconnect alarm
  else:
    continue ventilation
}

Figure 4:
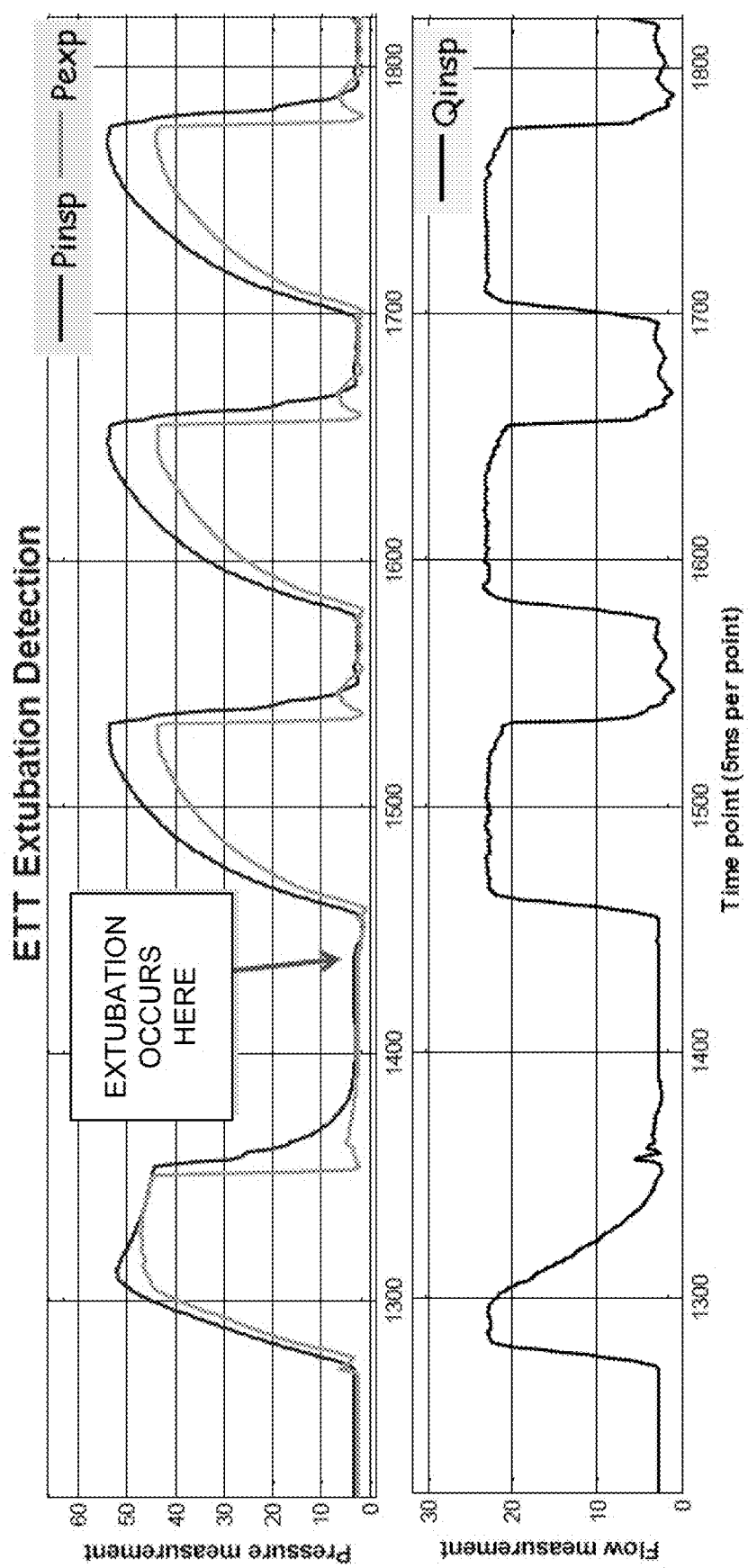
FIG. 4 depicts a simulated plot of ventilatory data after extubation of an ETT during ventilation in a pressure-controlled ventilation mode.

FIG. 4 depicts a simulated plot of ventilatory data after extubation of an ETT during ventilation in a pressure-controlled ventilation mode. More specifically, the simulated data shown in FIG. 4 is from the extubation of a neonatal ETT. The simulated data in FIGS. 4-7 was generated by providing ventilation to a set of artificial lungs with an ETT, and then extubating the ETT at the instance indicated in the figure. In the plot depicted in FIG. 4, the inspiratory periods occur between approximately time points 1280-1350, 1450-1540, 1580-1660, and 1700-1790. At the end of the inspiratory period prior to extubation, the inspiratory sensor pressure ($P_{insp}$) and the expiratory sensor pressure ($P_{exp}$) are relatively close to one another due the ETT tube being properly intubated. Once the ETT tube has been extubated, pressure still continues to build within the patient circuit, such as in the expiratory limb where the $P_{exp}$ is measured in this example. The pressure continues to build due to the resistance of the ETT tube itself. For example, the flow ($Q_{insp}$) during the inspiratory phases remains higher than the flow of gas that can escape through the ETT, thus causing a rise in pressure. As can be seen from the plot, at the end of an inspiratory period after extubation, the inspiratory sensor pressure ($P_{insp}$) is higher than the expiratory sensor pressure ($P_{exp}$) after extubation. Such a result is caused by the ETT tube having been extubated and allowing breathing gas to escape (or leak from) the patient circuit. In addition, due to the extubation of the ETT, the average flow over the inspiratory period after extubation is also higher than during inspiratory periods prior to extubation. Because the ventilator is in a pressure-controlled mode, additional flow is required to reach the desired pressure target. As such, a higher volume of breathing gas is provided by the ventilator after extubation. Further, because the breaths may be triggered by pressure indications dropping below a particular level, breaths are generated more rapidly following extubation. For example, the extubated ETT allows breathing gas to exit the patient circuit, resulting in a pressure drop following inspiration, thus triggering another breath.

Figure 5:
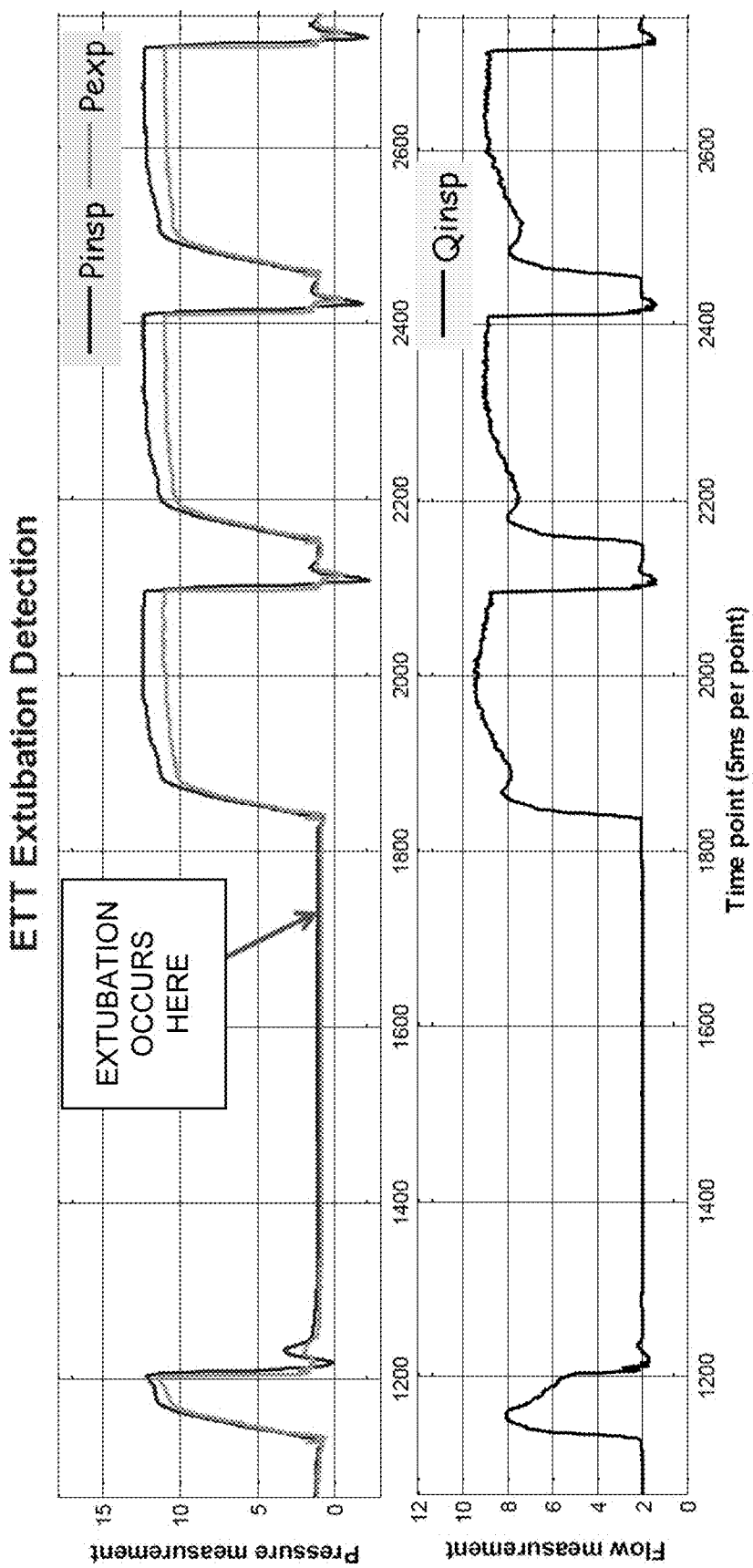
FIG. 5 depicts a simulated plot of ventilatory data after extubation of an ETT during ventilation in a pressure-support ventilation mode.

FIG. 5 depicts a simulated plot of ventilatory data after extubation of an ETT during ventilation in a pressure-support ventilation mode using a neonatal ETT. In the plot depicted in FIG. 5, the inspiratory periods occur between approximately time points 1100-1210, 1850-2100, 2160-2410, 2470-2720. As can be seen from the plot, at the end of an inspiratory period, the inspiratory sensor pressure ($P_{insp}$) is higher than the expiratory sensor pressure ($P_{exp}$) after extubation, similar to the plot in FIG. 4. Also similar to the plot in FIG. 4, the average flow provided during each inspiratory phase after extubation is higher than the average flow delivered in an inspiratory phase prior to extubation. The additional flow and the frequency of breaths are due to similar factors as those described above with respect to FIG. 4. Unlike the plot in FIG. 4, however, the duration of the inspiratory flow is also higher following extubation, causing a larger volume of breathing gas to be delivered by the ventilator than was provided prior to extubation The reason for the change in duration is based on the ventilator mode. In the pressure-support mode (FIG. 5), the inspiratory periods do not have a fixed duration, whereas in a pressure-controlled mode (FIG. 4), the inspiratory periods do have a fixed duration.

Figure 6:
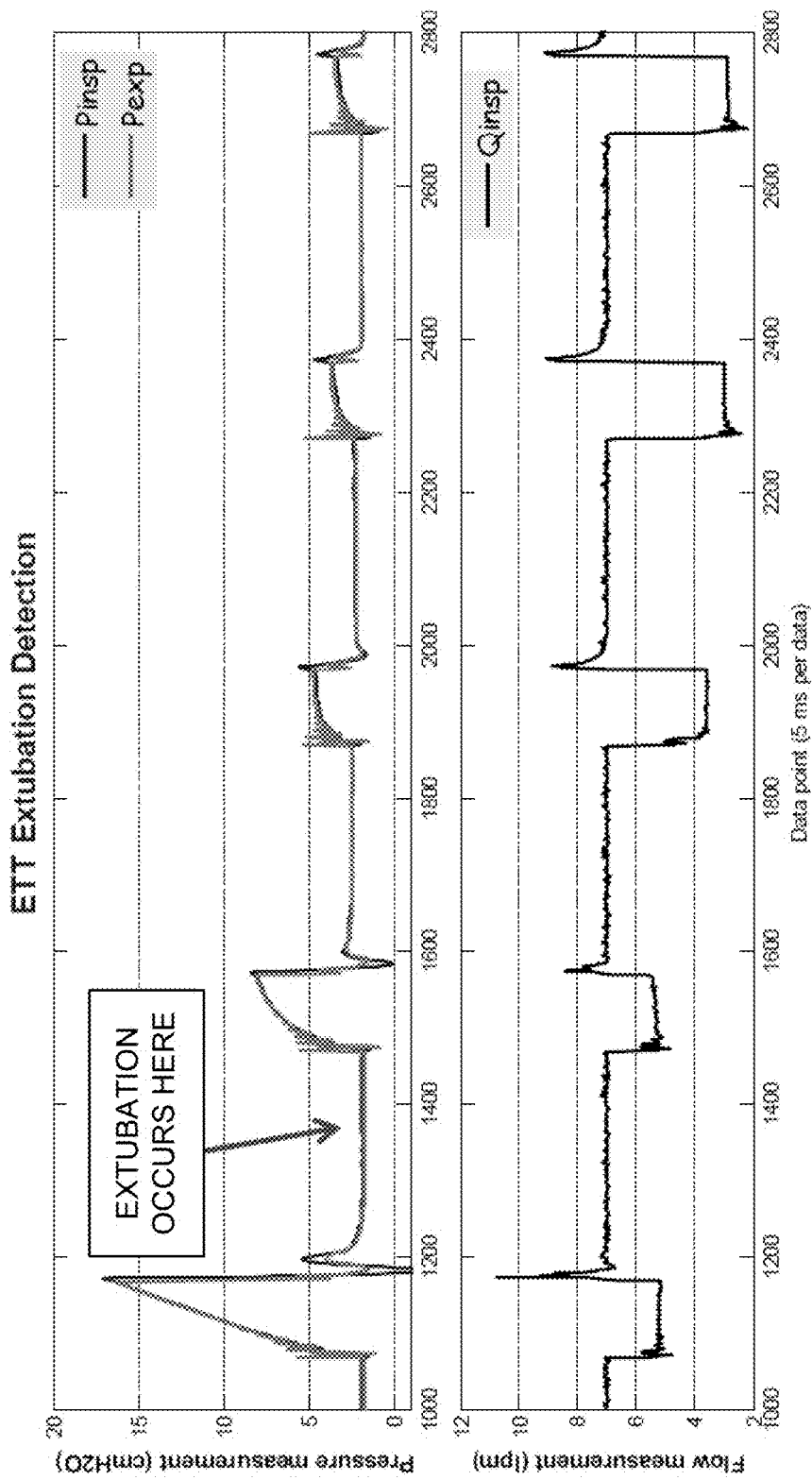
FIG. 6 depicts a simulated plot of ventilatory data after extubation of an ETT during ventilation in a volume-controlled ventilation mode.

FIG. 6 depicts a simulated plot of ventilatory data after extubation of an ETT during ventilation in a volume-controlled ventilation mode. In the plot depicted in FIG. 6, the inspiratory periods occur between approximately time points 1080-1180, 1480-1580, 1880-1980, 2280-2380, 2680-2780. During a volume-controlled ventilation mode, flow is controlled based on a tidal volume value that may be set by a medical provider via an interface on the ventilator. The inspiratory time is calculated based on the set tidal volume value and the set maximum flow value. Accordingly, the inspiratory time is constant when providing volume-controlled ventilation. During the expiratory phase, a base inspiratory flow ($Q_{insp}$) is provided to allow for triggering. In some embodiments, such as the one depicted in FIG. 6, the flow provided during exhalation is approximately 7 liters per minute (lpm). The inspiratory flow provided during the expiratory phase, however, does not cause a significant rise in pressure because the exhalation valve is open during the expiratory phase. Upon initiation of an inspiratory phase, the exhalation valve closes and the inspiratory flow is altered to provide the determined inspiratory flow for the patient. For instance, in the inspiratory phase prior to extubation, flow is reduced to approximately 5 lpm. The same inspiratory flow is provided by the ventilator in the first inspiratory period following extubation because the ventilator has not yet detected any differences. Because the ETT has been extubated, however, some of the inspiratory flow escapes the patient circuit, resulting in both a lower inspiratory sensor pressure ($P_{insp}$) and expiratory sensor pressure ($P_{exp}$) than resulting from a properly-intubated ETT tube. Such a result is also consistent with equation 7, above. After extubation, since the same combined higher $Q_{lung}$ and $V_{lung}$ are maintained to meet the determined tidal volume, and $E_{rs}$ has a decreased value, $P_{vent}$ also decreases.

In inspiratory phases following the first inspiratory phase after extubation, the inspiratory flow decreases during the inspiratory phases. For example, in the inspiratory phase from time points 1880-1980, the inspiratory flow provided in approximately 3.5 lpm, whereas the inspiratory flow delivered during the inspiratory phase between time points 1480-1580 was approximately 5 lpm. The drop in inspiratory flow is due to the ventilator compensating for the breathing gas being able to escape through the extubated ETT. The ventilator, in some embodiments, perceives the escaping air as additional compliance in the patient circuit. Based on the perceived change in compliance, the inspiratory flow delivered during the inspiratory phase is altered. The inspiratory flow is gradually altered until reaching a minimum flow of approximately 3 lpm in the depicted example. As the inspiratory flow reduces, the pressures ($P_{insp}$, $P_{exp}$) similarly reduce in amplitude.

Figure 7:
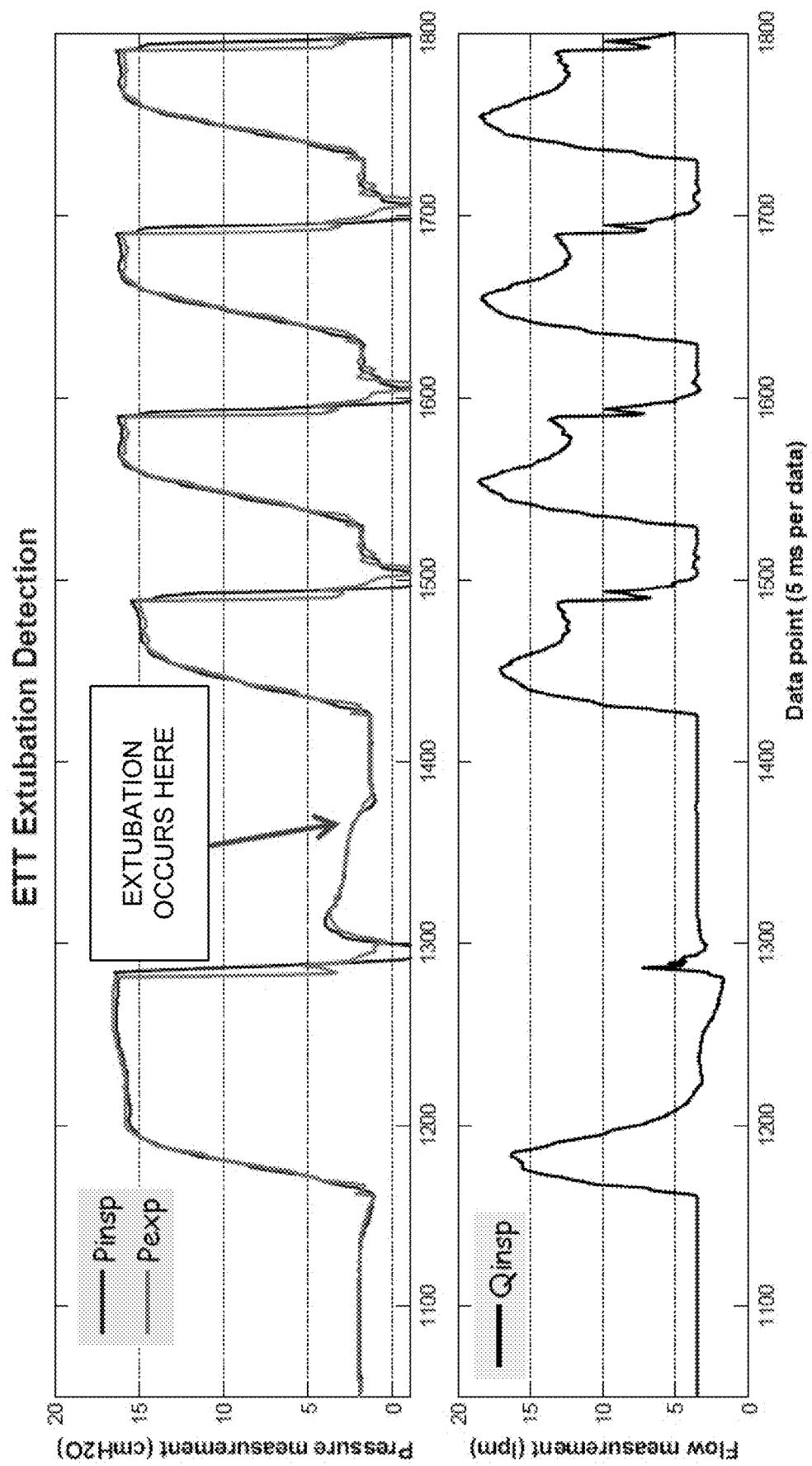
FIG. 7 depicts a simulated plot of ventilatory data after extubation of an ETT during ventilation in a volume-support ventilation mode.

FIG. 7 depicts a simulated plot of ventilatory data after extubation of an ETT during ventilation in a volume-support mode. During a volume-support mode, spontaneous breaths are delivered based on a volume support value, which may be provided by a medical provider via an interface on the ventilator. The inspiratory flow is generally controlled based on the set tidal volume value and there is no set duration for the inspiratory period, unlike in a volume-controlled mode. In some pressure-support mode embodiments, pressure may also be controlled based on the set tidal volume and estimated system compliance. As can be seen in the plot in FIG. 7, additional inspiratory flow is provided following extubation, resulting in a higher volume of breathing gas being delivered by the ventilator. The inspiratory flow increase following the extubation is due to trying to reach a particular pressure target. As discussed above with respect to FIGS. 4-5, additional inspiratory flow is required to reach a pressure target following extubation of an ETT.

In some embodiments, a microprocessor-based ventilator that accesses a computer-readable medium having computer-executable instructions for performing the method of ventilating a patient with a medical ventilator is disclosed. This method includes repeatedly performing the steps disclosed in method 200 above and/or as illustrated in FIGS. 2A-D. In some embodiments, this method includes repeatedly performing the steps disclosed in method 200 and method 300 above and/or as illustrated in FIGS. 2A-D and FIG. 3.

Those skilled in the art will recognize that the methods and systems of the present disclosure may be implemented in many manners and as such are not to be limited by the foregoing exemplary embodiments and examples. In other words, functional elements being performed by a single or multiple components, in various combinations of hardware and software or firmware, and individual functions, can be distributed among software applications either locally or remote through network connections. In this regard, any number of the features of the different embodiments described herein may be combined into single or multiple embodiments, and alternate embodiments having fewer than or more than all of the features herein described are possible. Functionality may also be, in whole or in part, distributed among multiple components, in manners now known or to become known. Thus, myriad software, hardware, firmware combinations are possible in achieving the functions, features, interfaces and preferences described herein.

Further, as used herein, "about" refers to a degree of deviation based on experimental error typical for the particular property identified. The latitude provided the term "about" will depend on the specific context and particular property and can be readily discerned by those skilled in the art. The term "about" is not intended to either expand or limit the degree of equivalents which may otherwise be afforded a particular value. Further, unless otherwise stated, the term "about" shall expressly include "exactly," consistent with the discussions regarding ranges and numerical data. Amounts and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 4 percent to about 7 percent" should be interpreted to include not only the explicitly recited values of about 4 percent to about 7 percent, but also include individual values and sub-ranges within the indicated range. Thus, included in this numerical range are individual values such as 4.5, 5.25 and 6 and sub-ranges such as from 4-5, from 5-7, and from 5.5-6.5; etc. This same principle applies to ranges reciting only one numerical value. Furthermore, such an interpretation should apply regardless of the breadth of the range or the characteristics being described.

Numerous other changes may be made which will readily suggest themselves to those skilled in the art and which are encompassed in the spirit of the disclosure and as defined in the appended claims. While various embodiments have been described for purposes of this disclosure, various changes and modifications may be made which are well within the scope of the present invention. Numerous other changes may be made which will readily suggest themselves to those skilled in the art and which are encompassed in the spirit of the disclosure and as defined in the claims.

What is claimed is:

1. A ventilator-implemented method for detecting extubation of an endotracheal tube during ventilation, the method comprising:
   determining, by the ventilator based on measurements from one or more sensors, a first volume of breathing gas delivered to a patient during a first inspiratory period;
   determining, by the ventilator based on measurements from the one or more sensors, a second volume of breathing gas delivered to a patient during a second inspiratory period;
   determining, by the ventilator, a difference between the first volume and the second volume;
   comparing, by the ventilator, the determined value for the difference between the first volume and the second volume to a threshold; and
   activating, by the ventilator, an alarm indicating extubation of the endotracheal tube when the determined value for the difference is greater than the threshold.

2. The method of claim 1, further comprising:
   measuring, by an inspiratory sensor, a first inspiratory pressure at the end of the first inspiratory period;
   measuring, by an expiratory sensor, a first expiratory pressure at the end the first inspiratory period;
   determining a first difference between the first inspiratory pressure measurement and the first expiratory pressure measurement;
   measuring a second inspiratory pressure at the end of the second inspiratory period;
   measuring a second expiratory pressure at the end of the second inspiratory period;
   determining a second difference between the second inspiratory pressure measurement and the second expiratory pressure measurement;
   comparing the first difference between the first inspiratory pressure measurement and the first expiratory pressure measurement to the second difference between the second inspiratory pressure measurement and the second expiratory pressure measurement; and
   wherein the alarm is activated only if the first difference between the first inspiratory pressure measurement and the first expiratory pressure measurement is less than the second difference between the second inspiratory pressure measurement and the second expiratory pressure measurement.

3. The method of claim 2, further comprising:
   measuring a first time duration of the first inspiratory period;
   measuring a second time duration of the second inspiratory period;
   wherein the alarm is activated only if the first time duration is shorter than the second time duration.

4. The method of claim 1, further comprising:
measuring a first time duration of the first inspiratory period;
measuring a second time duration of the second inspiratory period;
wherein the alarm is activated only if the first time duration is shorter than the second time duration.

5. The method of claim 4, wherein the method is performed during pressure-support ventilation.

6. The method of claim 1, wherein the ventilator does not include an exhalation flow sensor.

7. The method of claim 1, wherein the endotracheal tube is a high-resistance neo-natal endotracheal tube.

8. The method of claim 1, wherein the predetermined threshold is within the range of 0.2 to 0.7.

9. The method of claim 2, wherein the inspiratory pressure sensor is located in an inspiratory limb.

10. A ventilator system comprising:
a pressure generating system adapted to generate a flow of breathing gas;
a ventilation tubing system including a patient interface for connecting the pressure generating system to a patient, wherein the ventilation tubing system further includes an inspiratory limb, an expiratory limb, an endotracheal tube, and a wye connecting the inspiratory limb, the expiratory limb, and the endotracheal tube;
an inspiratory flow sensor coupled to at least one of the pressure generating system and the ventilation tubing system;
an inspiratory pressure sensor coupled to the inspiratory limb;
an expiratory pressure sensor coupled to the expiratory limb;
an interface for displaying operational data for the ventilator system;
one or more processors operatively coupled to at least the inspiratory pressure sensor and the expiratory sensor; and
a memory operatively coupled to the one or more processors, wherein the memory includes instructions configured cause the ventilator system to perform a set of operations upon execution by the one or more processors, the set of operations comprising:
determining a first volume of the breathing gas delivered to a patient during a first inspiratory period;
determining a second volume of breathing gas delivered to a patient during a second inspiratory period;
determining a difference between the first volume and the second volume;
comparing a value for the determined difference between the first volume and the second volume to a threshold; and
activating an alarm in the interface indicating extubation of the endotracheal tube when the determined value for the difference is greater than the threshold.

11. The system of claim 10, wherein the set of operations further comprises:
measuring, by the inspiratory pressure sensor, a first inspiratory pressure at the end of the first inspiratory period;
measuring, by the expiratory pressure sensor, a first expiratory pressure at the end the first inspiratory period;
determining a first difference between the first inspiratory pressure measurement and the first expiratory pressure measurement;
measuring, by the inspiratory pressure sensor, a second inspiratory pressure at the end of the second inspiratory period;
measuring, by the expiratory pressure sensor, a second expiratory pressure at the end of the second inspiratory period;
determining a second difference between the second inspiratory pressure measurement and the second expiratory pressure measurement;
comparing the first difference between the first inspiratory pressure measurement and the first expiratory pressure measurement to the second difference between the second inspiratory pressure measurement and the second expiratory pressure measurement; and
wherein the alarm is activated only if the first difference between the first inspiratory pressure measurement and the first expiratory pressure measurement is less than the second difference between the second inspiratory pressure measurement and the second expiratory pressure measurement.

12. The system of claim 11, wherein the set of operations further comprises:
measuring a first time duration of the first inspiratory period;
measuring a second time duration of the second inspiratory period;
wherein the alarm is activated only if the first time duration is shorter than that second time duration.

13. The system of claim 12, wherein the ventilator system is configured to deliver pressure-support ventilation.

14. The system of claim 10, wherein the threshold is within the range of about 0.2 to 0.7.

15. The system of claim 10, wherein the endotracheal tube is a high-resistance neo-natal endotracheal tube.

* * * * *